(12) United States Patent
Webber et al.

(10) Patent No.: US 10,648,002 B2
(45) Date of Patent: May 12, 2020

(54) METHOD FOR CORRECTING A GENETIC SEQUENCE

(71) Applicant: REGENTS OF THE UNIVERSITY OF MINNESOTA, Minneapolis, MN (US)

(72) Inventors: Beau R. Webber, Minneapolis, MN (US); Mark J. Osborn, Minneapolis, MN (US); Jakub Tolar, Minneapolis, MN (US); Bruce R. Blazar, Golden Valley, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 240 days.

(21) Appl. No.: 15/820,653

(22) Filed: Nov. 22, 2017

(65) Prior Publication Data
US 2018/0142262 A1  May 24, 2018

Related U.S. Application Data

(60) Provisional application No. 62/425,405, filed on Nov. 22, 2016.

(51) Int. Cl.
| | | |
|---|---|---|
| *C12N 15/90* | (2006.01) | |
| *C12N 5/077* | (2010.01) | |
| *C12N 5/074* | (2010.01) | |
| *C12N 5/071* | (2010.01) | |
| *C07K 14/78* | (2006.01) | |
| *C12N 5/0789* | (2010.01) | |
| *C12N 15/10* | (2006.01) | |

(52) U.S. Cl.
CPC ............ *C12N 15/907* (2013.01); *C07K 14/78* (2013.01); *C12N 5/0629* (2013.01); *C12N 5/0647* (2013.01); *C12N 5/0652* (2013.01); *C12N 5/0656* (2013.01); *C12N 5/0696* (2013.01); *C12N 15/102* (2013.01); *C07K 2319/81* (2013.01); *C12N 2310/20* (2017.05); *C12N 2500/38* (2013.01); *C12N 2500/90* (2013.01); *C12N 2501/155* (2013.01); *C12N 2501/727* (2013.01); *C12N 2502/28* (2013.01); *C12N 2506/1307* (2013.01); *C12N 2506/45* (2013.01); *C12N 2510/00* (2013.01); *C12N 2533/54* (2013.01); *C12N 2760/18843* (2013.01)

(58) Field of Classification Search
None
See application file for complete search history.

(56) References Cited

U.S. PATENT DOCUMENTS

2018/0346933 A1* 12/2018 Kogut .................... C12N 15/11

OTHER PUBLICATIONS

Hainzl et al in "CRISPR/Cas9-mediated gene repair in the COL7A1 gene" (Journal of Investigative Dermatology, suppl. Supplement 2 136.9: S189. Elsevier B.V. (Sep. 2016). (Year: 2016).*
Shinkuma et al entitled "Site-specific genome editing using CRISPR/Cas9 and TALENs for correction of iPS cells derived from dominant dystrophic epidermolysis bullosa" (Abstract #419 to Gene Therapy & Clinical Therapeutics, The Journal of Investigative Dermatology 135.S1: S70-S73. London. May 2015). (Year: 2015).*
Thesis Dissertation of Emily Faith Ward, University of Minnesota, 2016). (Year: 2016).*
Ausubel, *Current Protocols in Molecular Biology, Supplement 30*. John Wiley & Sons, Inc.: Media, PA; 1987.
Bannwarth et al., "Surveyor™ Nuclease: A New Strategy for a Rapid Identification of Heteroplasmic Mitochondrial DNA Mutations in Patients With Respiratory Chain Defects" 2005 *Human Mutation*, 25:575-582.
Bonab et al., "Aging of mesenchymal stem cell in vitro" 2006 *BMC Cell Biol.*, 7:14 (7 pages).
Cermak et al., "Efficient design and assembly of custom TALEN and other TAL effector-based constructs for DNA targeting" 2011 *Nucleic Acids Research*, 39:e82 (11 pages).
Chamorro et al., "Gene Editing for the Efficient Correction of a Recurrent *COL7A1* Mutation in Recessive Dystrophic Epidermolysis Bullosa Keratinocytes" Apr. 2016 *Molecular Therapy—Nucleic Acids*, 5:e307 (13 pages).
Christian et al., "Targeting DNA Double-Strand Breaks with TAL Effector Nucleases" 2010 *Genetics*, 186:757-761.
Cong et al., "Multiplex Genome Engineering Using CRISPR/Cas Systems" 2013 *Science*, 339:819-823.
Conget et al., "Replenishment of type VII collagen and re-epithelialization of chronically ulcerated skin after intradermal administration of allogeneic mesenchymal stromal cells in two patients with recessive dystrophic epidermolysis bullosa" 2010 *Cytotherapy*, 12:429-431.
Ditadi et al., "Human definitive haemogenic endothelium and arterial vascular endothelium represent distinct lineages" 2015 *Nat. Cell Biol.*, 17(5):580-591 (including 7 pages Supplementary Information).
Dominici et la., "Minimal criteria for defining multipotent mesenchymal stromal cells: The International Society for Cellular Therapy position statement" 2006 *Cytotherapy*, 8(4):315-317.
Fine et la., "Extracutaneous manifestations and complications of inherited epidermolysis bullosa, Part II. Other organs" 2009 *J. Am. Acad. Dermatol.*, 61:387-402.
Fu et al., "Comparison of Immunological Characteristics of Mesenchymal Stem Cells Derived from Human Embryonic Stem Cells and Bone Marrow" 2015 *Tissue Eng Part A* 21(3-4):616-626.
Fujie et al., "New Type of Sendai Virus Vector Provides Transgene-Free iPS Cells Derived from Chimpanzee Blood" 2014 *PLoS One*, 9(12):e113052 (19 pages).

(Continued)

*Primary Examiner* — Catherine S Hibbert
(74) *Attorney, Agent, or Firm* — Mueting, Raasch & Gebhardt, P.A.

(57) ABSTRACT

Methods of gene correction, methods of generating induced pluripotent stem cells (iPSCs), and methods of deriving multi-lineage cell types with therapeutic value. In some embodiments, the gene correction affects the expression and/or function of the functional type VII collagen protein (C7).

20 Claims, 18 Drawing Sheets
(16 of 18 Drawing Sheet(s) Filed in Color)
Specification includes a Sequence Listing.

(56) References Cited

OTHER PUBLICATIONS

Fujita et al., "Bone marrow transplantation restores epidermal basement membrane protein expression and rescues epidermolysis bullosa model mice" 2010 *Proc Natl Acad Sci USA*, 107(32):14345-14350.
Genovese et al., "Targeted Genome Editing in Human Repopulating Haematopoietic Stem Cells" 2014 *Nature* 510(7504):235-240.
Georgiadis et al., "Lentiviral Engineered Fibroblasts Expressing Codon-Optimized *COL7A1* Restore Anchoring Fibrils in RDEB" 2016 *J Invest Dermatol.*, 136:284-292 (published online Sep. 22, 2015).
Gibson et al., "Enzymatic assembly of DNA molecules up to several hundred kilobases" 2009 *Nat Methods* 6(5):343-345.
Gori et al., "Vascular niche promotes hematopoietic multipotent progenitor formation from pluripotent stem cells" 2015 *J. Clin. Invest.*, 125(3):1243-1254.
Goto et al., "Fibroblasts Show More Potential as Target Cells than Keratinocytes in COL7A1 Gene Therapy of Dystrophic Epidermolysis Bullosa" 2006 *J. Invest. Dermatol.*, 126:766-772.
Guschin et al., "A Rapid and General Assay for Monitoring Endogenous Gene Modification" 2010 *Methods in Molecular Biology*, 649:247-256.
Hacein-Bey-Abina et al., "Insertional oncogenesis in 4 patients after retrovirus-mediated gene therapy of SCID-X1" 2008 *J. Clin. Invest.*, 118:3132-3142.
Heyer et al., "Regulation of homologous recombination in eukaryotes" 2010 *Annu. Rev. Genet.*, 44:113-139.
Hoban et al., "Correction of the sickle cell disease mutation in human hematopoietic stem/progenitor cells" 2015 *Blood*, 125:2597-2604.
Itoh, "Generation of keratinocytes from normal and recessive dystrophic epidermolysis bullosa-induced pluripotent stem cells" 2011 *Proc Natl Acad Sci USA*, 108(21):8797-8802.
Izmiryan et al., "Meganuclease-Mediated *COL7A1* Gene Correction for Recessive Dystrophic Epidermolysis Bullosa" Apr. 2016 *J Invest Dermatol.*, 136:872-875.
Jacobs et al., "Immunological characteristics of human mesenchymal stem cells and multipotent adult progenitor cells" 2013 *Immunol Cell Biol.*, 91:32-39.
Kennedy et al., "T Lymphocyte Potential Marks the Emergence of Definitive Hematopoietic Progenitors in Human Pluripotent Stem Cell Differentiation Cultures" 2012 *Cell Rep.*, 2:1722-1735.
Kogut et al., "Differentiation of Human Induced Pluripotent Stem Cells into a Keratinocyte Lineage" 2014 *Methods Mol Biol.*, 1195:1-12.
Kuhl et al., "High Local Concentrations of Intradermal MSCs Restore Skin Integrity and Facilitate Wound Healing in Dystrophic Epidermolysis Bullosa" 2015 *Mol Ther.*, 23(8):1368-1379.
Latifi-Pupovci et al., "In vitro migration and proliferation ("wound healing") potential of mesenchymal stromal cells generated from human CD271+ bone marrow mononuclear cells" 2015 *J Transl Med.*, 13:315 (9 pages).
Lian et al., "Functional Mesenchymal Stem Cells Derived From Human Induced Pluripotent Stem Cells Attenuate Limb Ischemia in Mice" 2010 *Circulation*, 121:1113-1123 (including Supplemental Material).
Lin et al., "Enhanced homology-directed human genome engineering by controlled timing of CRISPR/Cas9 delivery" 2014 *eLife*, 3:e04766 (13 pages).
Mali et al., "RNA-Guided Human Genome Engineering via Cas9" 2013 *Science*, 339:823-826.
Mavilio et al., "Correction of junctional epidermolysis bullosa by transplantation of genetically modified epidermal stem cells" 2006 *Nat Med.*, 12:1397-1402.
Nakagawa et al., "Generation of induced pluripotent stem cells without Myc from mouse and human fibroblasts" 2008 *Nat. Biotechnol.*, 26(1):101-6.
National Center for Biotechnology Information, National Library of Medicine, National Institutes of Health, GenBank Locus HUMCD34HS, Accession No. M81104 X60172, "*Homo sapiens* CD34 mRNA, complete cds," [online]. Bethesda, MD. Retrieved from the Internet [on Jul. 17, 2018]: https://www.ncbi.nlm.nih.gov/nuccore/m81104 (2 pages).
Ng et al., "A protocol describing the use of a recombinant protein-based, animal product-free medium (APEL) for human embryonic stem cell differentiation as spin embryoid bodies" 2008 *Nat Protoc.*, 3(5):768-776.
Okita et al., "Generation of germline-competent induced pluripotent stem cells" 2007 *Nature*, 448:313-317.
Osborn et al., "TALEN-based Gene Correction for Epidermolysis Bullosa" 2013 *Mol Ther.*, 21(6):1151-1159.
Osborn et al., "Fanconi Anemia Gene Editing by the CRISPR/Cas9 System" 2015 *Hum. Gene Ther.*, 26:114-126.
Osborn et al., "371 CRISPR/Cas9 genetic correction for recessive dystrophic epidermolysis bullosa (RDEB)" May 2016 *Journal of Investigative Dermatology*, 136(5):S66.
Osborn et al., "CRISPR/Cas9-based genetic correction for recessive dystrophic epidermolysis bullosa (RDEB)" (Poster # 371), Friday, May 13, 2016, "Annual Society of Investigative Dermatology Meeting" Scottsdale, AZ, May 11-14, 2018; 92 pages.
Osborn et al., "CRISPR/Cas9 Targeted Gene Editing and Cellular Engineering in Fanconi Anemia" 2016 *Stem Cells Dev.*, 25(20):1591-1603 (published online Aug. 18, 2016).
Paques et al., "Meganucleases and DNA double-Strand Break-Induced Recombination: Perspectives for Gene Therapy" 2007 *Curr. Gene Ther.*, 7:49-66.
Petrof et al., "Fibroblast cell therapy enhances initial healing in recessive dystrophic epidermolysis bullosa wounds: results of a randomized, vehicle-controlled trial" 2013 *Br. J. Dermatol.*, 169:1025-1033.
Petrof, "Potential of Systemic Allogeneic Mesenchymal Stromal Cell Therapy for Children with Recessive Dystrophic Epidermolysis Bullosa" 2015 *J Invest Dermatol.*, 135(9):2319-2321.
Porteus et al., "Gene targeting using zinc finger nucleases" 2005 *Nat Biotechnol.*, 23(8):967-973.
Rossant, "Stem cells: The magic brew" 2007 *Nature*, 448:260-262.
Sandler et al., "Reprogramming Human Endothelial Cells to Haematopoietic Cells Requires Vascular Induction" 2014 *Nature*, 511(7509):312-318.
Sasaki et al., "Mesenchymal Stem Cells Are Recruited Into Wounded Skin and Contribute to Wound Repair by Transdifferentiation into Multiple Skin Cell Type." 2008 *J Immunol* 180:2581-2587.
Schmitt et al, "Induction of T Cell Development from Hematopoietic Progenitor Cells by Delta-like-1 In Vitro" 2002 *Immunity*, 17:749-756.
Schmitt et al, "Induction of T cell development and establishment of T cell competence from embryonic stem cells differentiated *in vitro*" 2004 *Nat Immunol.*, 5:410-417.
Schwarz, "Bone marrow-derived mesenchymal stem cells migrate to healthy and damaged salivary glands following stem cell infusion" 2014 *Int. J. Oral Sci.*, 6:154-161.
Sebastiano et al., "Human *COL7A1*—corrected induced pluripotent stem cells for the treatment of recessive dystrophic epidermolysis bullosa" 2014 *Sci. Transl. Med.*, 6(264):264ra163 (13 pages).
Shen et al., "Efficient genome modification by CRISPR-Cas9 nickase with minimal off-target effects" 2014 *Nat Methods*, 11(4):399-402 (including Online Methods).
Stelzl et al., "A human protein-protein interaction network: a resource for annotating the proteome" 2005 *Cell* 122:957-968.
Sturgeon et al., "Wnt signaling controls the specification of definitive and primitive hematopoiesis from human pluripotent stem cells" 2014 *Nat. Biotechnol.* 32(6):554-561.
Takahashi et al., "Induction of Pluripotent Stem Cells from Mouse Embryonic and Adult Fibroblast Cultures by Defined Factors" 2006 *Cell*, 126:663-76.
Takahashi et al., "Induction of Pluripotent Stem Cells from Adult Human Fibroblasts by Defined Factors" 2007 *Cell*, 131:861-872.
Tolar et al., "Amelioration of epidermolysis bullosa by transfer of wild-type bone marrow cells" 2009 *Blood*, 113(5):1167-1174.

(56) References Cited

OTHER PUBLICATIONS

Tolar et al., "Induced Pluripotent Stem Cells from Individuals with Recessive Dystrophic Epidermolysis Bullosa" 2011 *J. Invest. Dermatol.*, 131(4):848-856.
Tolar et al., "Keratinocytes from Induced Pluripotent Stem Cells in Junctional Epidermolysis Bullosa" 2013 *J. Invest. Dermatol.*, 133(2):562-565.
Tolar et al., "A Biologic Velcro Patch" 2015 *N. Engl. J. Med.*, 372(4):382-384.
Tolar et al., "263 Skin engraftment and type VII collagen (C7) expression after allogeneic hematopoietic cell transplantation (HCT) for generalized severe recessive dystrophic epidermolysis bullosa (RDEB)" May 2016 *Journal of Investigative Dermatology*, 136(5):S46.
Umegaki-Arao et al., "Induced pluripotent stem cells from human revertant keratinocytes for the treatment of epidermolysis bullosa" 2014 *Sci. Transl. Med.* 6(264):264ra164 (11 pages).
Van Den Akker et al., "The International Dystrophic Epidermolysis Bullosa Patient Registry: An Online Database of Dystrophic Epidermolysis Bullosa Patients and Their COL7A1 Mutations" 2011 *Hum Mutat.*, 32:1100-1107.
Vanden Oever, "390 miR-29 regulates type VII collagen in individuals with recessive dystrophic epidermolysis bullosa (RDEB)" May 2016 *Journal of Investigative Dermatology*, 136(5):S69.
Vanden Oever, "miR-29 Regulates Type VII Collagen in Recessive Dystrophic Epidermolysis Bullosa" 2016 *J Invest Dermatol.*, 136(10):2013-2021 (published online Jun. 18, 2016).
Van Rensburg et al., "Chromatin structure of two genomic sites for targeted transgene integration in induced pluripotent stem cells and hematopoietic stem cells" 2013 *Gene Ther.*, 20:201-214.
Wagner, "Bone Marrow Transplantation for Recessive Dystrophic Epidermolysis Bullosa" 2010 *N. Engl. J. Med.*, 363:629-639.
Wang, "Homology-driven genome editing in hematopoietic stem and progenitor cells using ZFN mRNA and AAV6 donors" 2015 *Nat. Biotechnol.* 33(12):1256-1263.
Webber et al., "419 Efficient CRISPR/Cas9-mediated knockout of Col7a1 in NOD/SCID IL2Rgamma-null mice by pro-nuclear injection" May 2016 *Journal of Investigative Dermatology*, 136(5):S74.
Webber et al., "CRISPR/Cas9-based genetic correction for recessive dystrophic epidermolysis bullosa" 2016 *NPJ Regen. Medicine*, 16014 (11 pages) (published online Dec. 8, 2016).
Wenzel et al., "Genetically corrected iPSCs as cell therapy for recessive dystrophic epidermolysis bullosa" 2014 *Sci. Transl. Med.*, 6(264):264ra165.
Woodley et al., "Intradermal Injection of Lentiviral Vectors Corrects Regenerated Human Dystrophic Epidermolysis Bullosa Skin Tissue *in Vivo*" 2004 *Mol. Ther.*, 10(2):318-326.
Wu et al., "Mesenchymal Stem Cells Enhance Wound Healing Through Differentiation and Angiogenesis" 2007 *Stem Cells*, 25:2648-2659.
Yu et al., "Induced pluripotent stem cell lines derived from human somatic cells" 2007 *Science* 318(5858):1917-20.
Yu et al., "Human Induced Pluripotent Stem Cells Free of Vector and Transgene Sequences" 2009 *Science* 324(5928):797-801.

\* cited by examiner

Figure 5
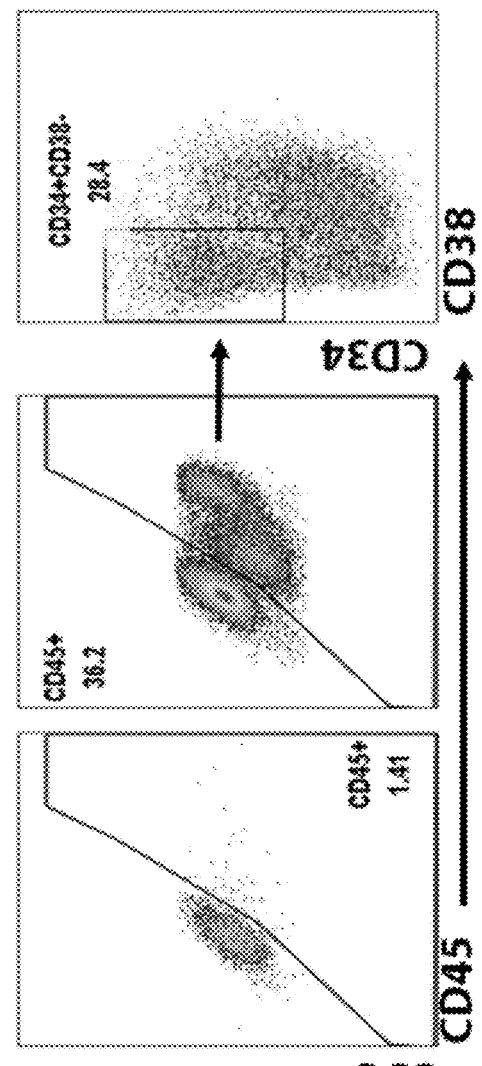
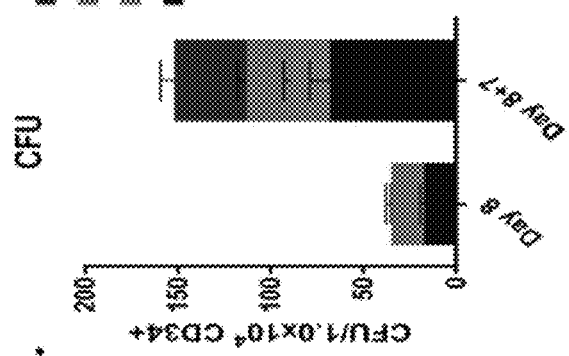
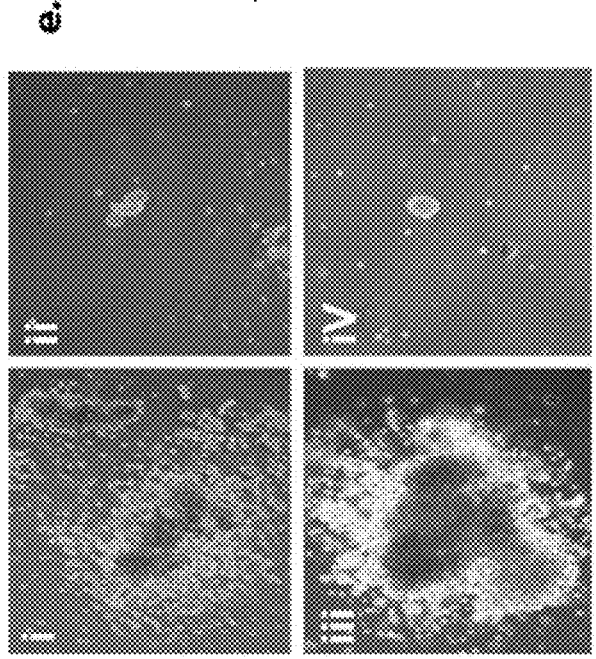

Figure 6
A. GTGCTGGGCTTCATAGTTCTTGG[N34]CCGGAAGCCCTGGACCCCAAGGCCCGTTGG[C][N63]GGAGGCTGCGTGCTGGGGGCAGG
B. gRNA 1: GTGCTGGGCTTCATAGTTCT TGG
   gRNA 2: GGAGGCTGCCTGCTGGGGC AGG
   gRNA 3: GCCTTGGGGGTCCAGGGCTTC CGG
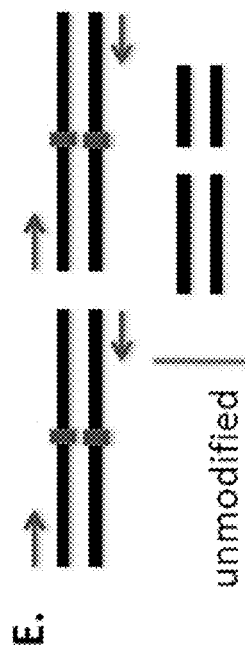
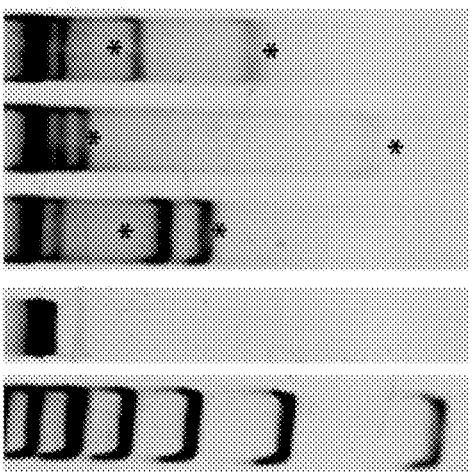
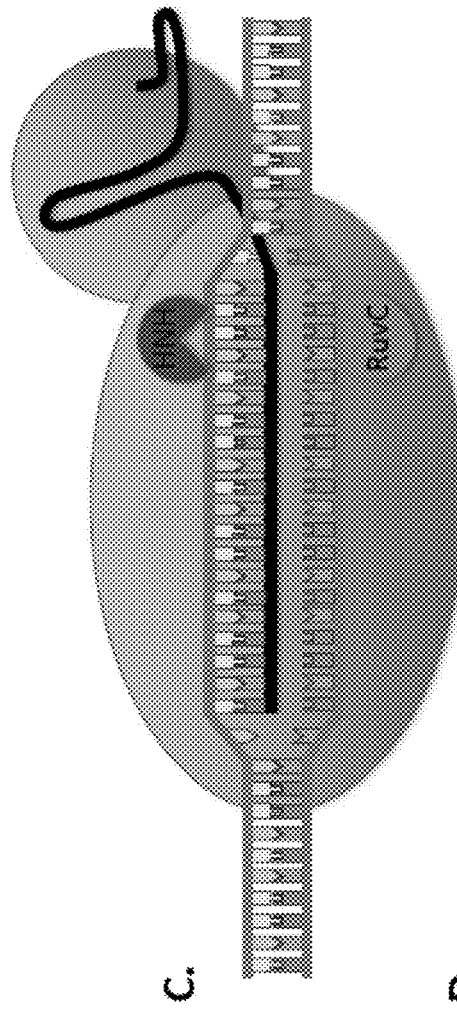

Figure 8
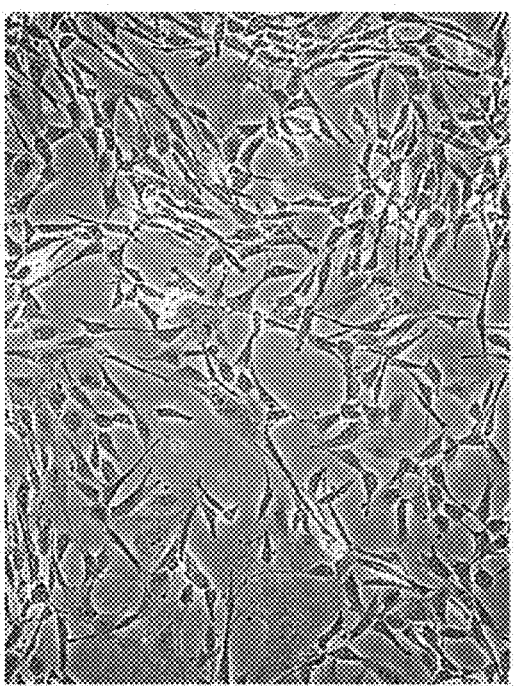
A.
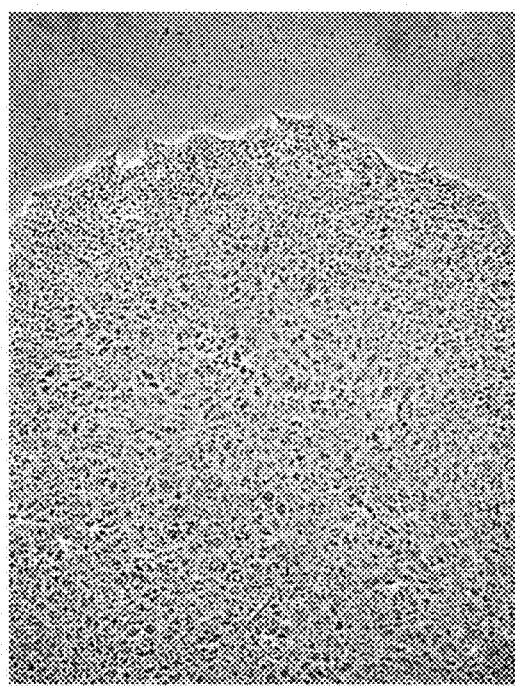
C.
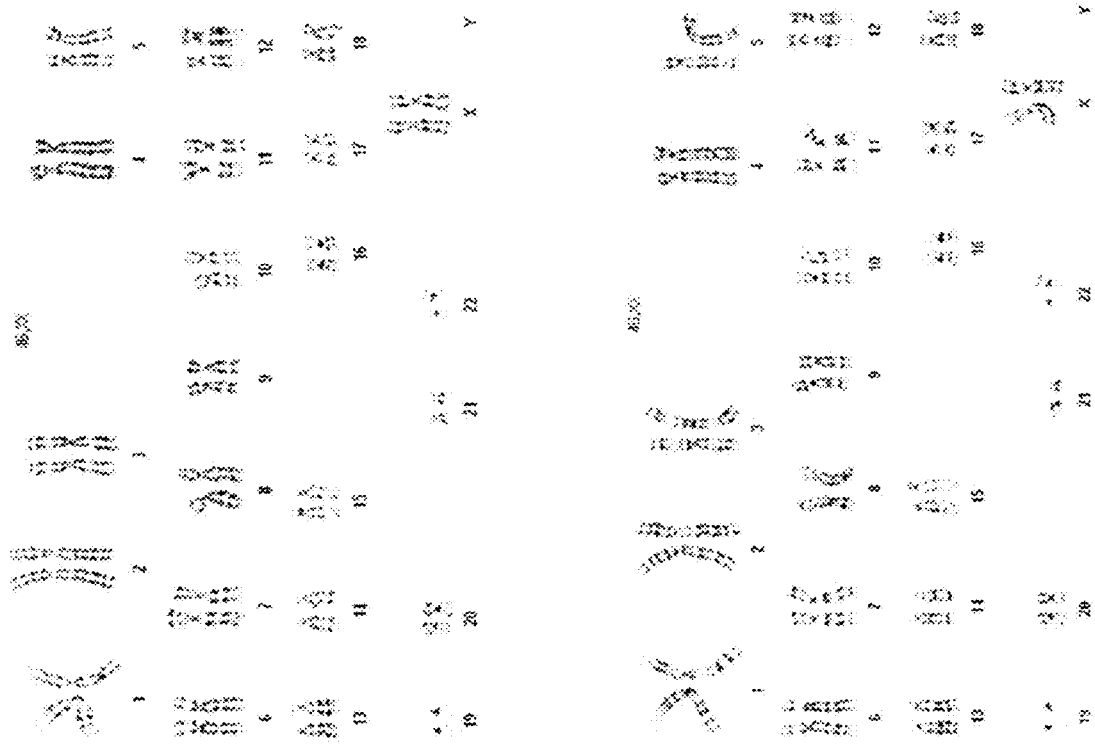
B.
D.

SEQUENCE LISTING

<160> NUMBER OF SEQ ID NOS: 63

<210> SEQ ID NO 1
<211> LENGTH: 29
<212> TYPE: DNA
<213> ORGANISM: artificial
<220> FEATURE:
<223> OTHER INFORMATION: primer

<400> SEQUENCE: 1
cctgacctct tcacctcctc agggcttcc                                29

<210> SEQ ID NO 2
<211> LENGTH: 30
<212> TYPE: DNA
<213> ORGANISM: artificial
<220> FEATURE:
<223> OTHER INFORMATION: primer

<400> SEQUENCE: 2
gggccacacc tcactcccaa agataccagg                               30

<210> SEQ ID NO 3
<211> LENGTH: 32
<212> TYPE: DNA
<213> ORGANISM: artificial
<220> FEATURE:
<223> OTHER INFORMATION: primer

<400> SEQUENCE: 3
agggtcatgg ggtcgtcatc tgttttctag gg                            32

<210> SEQ ID NO 4
<211> LENGTH: 35
<212> TYPE: DNA
<213> ORGANISM: artificial
<220> FEATURE:
<223> OTHER INFORMATION: primer

<400> SEQUENCE: 4
aactatgaag cccagcaccc aaccactgcc ccagg                         35

<210> SEQ ID NO 5
<211> LENGTH: 241
<212> TYPE: DNA
<213> ORGANISM: artificial
<220> FEATURE:
<223> OTHER INFORMATION: primer

<400> SEQUENCE: 5
ctctcctggg gcagtggttg ggtgctgggc ttcatagttc ttgctcatat ttttactcac    60
ttcttcctag ggtcttcctg gcagccctgg accccaaggc ccgttggcc ccctggaaa    120 gaaaggagaa aaagtaggaa ggctgacttg atgatgtccc agttctgggg tgggaggctg   180
cgtgctgggg gcagcctccc ttcggtcttc ccaccgtgt gtttctcctt cagggtgact    240
c                                                                   241

<210> SEQ ID NO 6
<211> LENGTH: 30
<212> TYPE: DNA
<213> ORGANISM: artificial
<220> FEATURE:
<223> OTHER INFORMATION: primer

<400> SEQUENCE: 6

```
cacccgtgtg tttctccttc agggtgactc                                      30
```

<210> SEQ ID NO 7
<211> LENGTH: 32
<212> TYPE: DNA
<213> ORGANISM: artificial
<220> FEATURE:
<223> OTHER INFORMATION: primer

<400> SEQUENCE: 7

```
gggcaagaag tcagaaccag aaagggcaca gc                                   32
```

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8

```
ccatgaccct catcactcct                                                 20
```

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9

```
tttgggggtt cagagatttg                                                 20
```

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10

```
tcccaaagtc cttgaaatcc                                                 20
```

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11

```
gcccaccata ttcagaatcc                                                 20
```

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12

```
acggccttgt acagaactgg                                                 20
```

<210> SEQ ID NO 13
<211> LENGTH: 20
<212> TYPE: DNA

```
<213> ORGANISM: artificial
<220> FEATURE:
<223> OTHER INFORMATION: primer

<400> SEQUENCE: 13
gtgctttcgc tccatctcac                                               20

<210> SEQ ID NO 14
<211> LENGTH: 20
<212> TYPE: DNA
<213> ORGANISM: artificial
<220> FEATURE:
<223> OTHER INFORMATION: primer

<400> SEQUENCE: 14
ccagaggagc cttgagtttg                                               20

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
ctacccagcc cccttacttc                                               20

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
tggtacgtcg agggtcctaa                                               20

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
ccttggaggc tactgacagc                                               20

<210> SEQ ID NO 18
<211> LENGTH: 20
<212> TYPE: DNA
<213> ORGANISM: artificial
<220> FEATURE:
<223> OTHER INFORMATION: primer

<400> SEQUENCE: 18
gctacctctc ctccctcctc                                               20

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
ccaccgtttt ccacatcttt                                               20
```

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
ggctcatccg taacctgcta                                          20

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
gggcaacctg gagatacaga                                          20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
ttttgtcgag atggggtctc                                          20

<210> SEQ ID NO 23
<211> LENGTH: 20
<212> TYPE: DNA
<213> ORGANISM: artificial
<220> FEATURE:
<223> OTHER INFORMATION: primer

<400> SEQUENCE: 23
ggggacagtg cataatctgg                                          20

<210> SEQ ID NO 24
<211> LENGTH: 20
<212> TYPE: DNA
<213> ORGANISM: artificial
<220> FEATURE:
<223> OTHER INFORMATION: primer

<400> SEQUENCE: 24
agatgaacca catccccaag                                          20

<210> SEQ ID NO 25
<211> LENGTH: 20
<212> TYPE: DNA
<213> ORGANISM: artificial
<220> FEATURE:
<223> OTHER INFORMATION: primer

<400> SEQUENCE: 25
tggacaaggg taggcatagg                                          20

<210> SEQ ID NO 26
<211> LENGTH: 20
<212> TYPE: DNA
<213> ORGANISM: artificial
<220> FEATURE:

```
<223> OTHER INFORMATION: primer

<400> SEQUENCE: 26
aagaatcagg aagcccaggt                                              20

<210> SEQ ID NO 27
<211> LENGTH: 20
<212> TYPE: DNA
<213> ORGANISM: artificial
<220> FEATURE:
<223> OTHER INFORMATION: primer

<400> SEQUENCE: 27
gtctcaaaca gcccagcttc                                              20

<210> SEQ ID NO 28
<211> LENGTH: 20
<212> TYPE: DNA
<213> ORGANISM: artificial
<220> FEATURE:
<223> OTHER INFORMATION: primer

<400> SEQUENCE: 28
gagaccaagc tggaaagcac                                              20

<210> SEQ ID NO 29
<211> LENGTH: 20
<212> TYPE: DNA
<213> ORGANISM: artificial
<220> FEATURE:
<223> OTHER INFORMATION: primer

<400> SEQUENCE: 29
agctcagaac ctcaggacca                                              20

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
cattcctctc tgccaccttc                                              20

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
tgttcgccga ttcctttatt                                              20

<210> SEQ ID NO 32
<211> LENGTH: 20
<212> TYPE: DNA
<213> ORGANISM: artificial
<220> FEATURE:
<223> OTHER INFORMATION: primer

<400> SEQUENCE: 32
agaggtgaca cagccctcat                                              20
```

```
<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
agggtcttct cccagtcagg                                              20

<210> SEQ ID NO 34
<211> LENGTH: 20
<212> TYPE: DNA
<213> ORGANISM: artificial
<220> FEATURE:
<223> OTHER INFORMATION: primer

<400> SEQUENCE: 34
ctttgggtcc ctgttgagac                                              20

<210> SEQ ID NO 35
<211> LENGTH: 20
<212> TYPE: DNA
<213> ORGANISM: artificial
<220> FEATURE:
<223> OTHER INFORMATION: primer

<400> SEQUENCE: 35
gaagacgtgc tccatcccta                                              20

<210> SEQ ID NO 36
<211> LENGTH: 22
<212> TYPE: DNA
<213> ORGANISM: artificial
<220> FEATURE:
<223> OTHER INFORMATION: primer

<400> SEQUENCE: 36
gccactccca ctgtcctttc ct                                           22

<210> SEQ ID NO 37
<211> LENGTH: 20
<212> TYPE: DNA
<213> ORGANISM: artificial
<220> FEATURE:
<223> OTHER INFORMATION: primer

<400> SEQUENCE: 37
gggcaagaag tcagaaccag                                              20

<210> SEQ ID NO 38
<211> LENGTH: 18
<212> TYPE: DNA
<213> ORGANISM: artificial
<220> FEATURE:
<223> OTHER INFORMATION: primer

<400> SEQUENCE: 38
gtgacaaagg cgatcgtg                                                18

<210> SEQ ID NO 39
<211> LENGTH: 17
<212> TYPE: DNA
<213> ORGANISM: artificial
<220> FEATURE:
<223> OTHER INFORMATION: primer
```

```
<400> SEQUENCE: 39
gtccccgtgg gccctgc                                                    17

<210> SEQ ID NO 40
<211> LENGTH: 40
<212> TYPE: DNA
<213> ORGANISM: Homo sapiens

<400> SEQUENCE: 40
ccggaagccc tggaccccaa ggccccgttg gccccctgga                            40

<210> SEQ ID NO 41
<211> LENGTH: 40
<212> TYPE: DNA
<213> ORGANISM: Homo sapiens

<400> SEQUENCE: 41
ctggcagccc tggaccccaa ggccccgttg gccccctgga                            40

<210> SEQ ID NO 42
<211> LENGTH: 77
<212> TYPE: DNA
<213> ORGANISM: Homo sapiens

<400> SEQUENCE: 42
gtgctgggct tcatagttct tggccggaag ccctggaccc caaggcccgt tggcggaggc      60
tgcgtgctgg gggcagg                                                    77

<210> SEQ ID NO 43
<211> LENGTH: 23
<212> TYPE: DNA
<213> ORGANISM: artificial
<220> FEATURE:
<223> OTHER INFORMATION: polynucleotide

<400> SEQUENCE: 43
gtgctgggct tcatagttct tgg                                             23

<210> SEQ ID NO 44
<211> LENGTH: 23
<212> TYPE: DNA
<213> ORGANISM: artificial
<220> FEATURE:
<223> OTHER INFORMATION: polynucleotide

<400> SEQUENCE: 44
ggaggctgcg tgctgggggc agg                                             23

<210> SEQ ID NO 45
<211> LENGTH: 22
<212> TYPE: DNA
<213> ORGANISM: artificial
<220> FEATURE:
<223> OTHER INFORMATION: polynucleotide

<400> SEQUENCE: 45
gccttggggt ccaggcttcc gg                                              22

<210> SEQ ID NO 46
<211> LENGTH: 18
<212> TYPE: DNA
<213> ORGANISM: artificial
<220> FEATURE:
<223> OTHER INFORMATION: polynucleotide
```

<400> SEQUENCE: 46
aggtcagctg gtatgagc                                                     18

<210> SEQ ID NO 47
<211> LENGTH: 103
<212> TYPE: DNA
<213> ORGANISM: artificial
<220> FEATURE:
<223> OTHER INFORMATION: polynucleotide

<400> SEQUENCE: 47
ggcccggtat gtcgggaacc tctccagggg taccataact tcgtataatg tatgctatac      60
gaagttatct cgagggtatg tcgggaacct ctccaggagg gtc                       103

<210> SEQ ID NO 48
<211> LENGTH: 36
<212> TYPE: DNA
<213> ORGANISM: artificial
<220> FEATURE:
<223> OTHER INFORMATION: cDNA

<400> SEQUENCE: 48
tggcagccct ggaccccaag gccccgttgg cccccc                                 36

<210> SEQ ID NO 49
<211> LENGTH: 23
<212> TYPE: DNA
<213> ORGANISM: Homo sapiens

<400> SEQUENCE: 49
acaggctgca tgttgggggc tgg                                               23

<210> SEQ ID NO 50
<211> LENGTH: 23
<212> TYPE: DNA
<213> ORGANISM: Homo sapiens

<400> SEQUENCE: 50
gggggcctcg ggctgggggc tag                                               23

<210> SEQ ID NO 51
<211> LENGTH: 23
<212> TYPE: DNA
<213> ORGANISM: Homo sapiens

<400> SEQUENCE: 51
gggggcaggc tgctgggggc agg                                               23

<210> SEQ ID NO 52
<211> LENGTH: 23
<212> TYPE: DNA
<213> ORGANISM: Homo sapiens

<400> SEQUENCE: 52
ggcggcggcg ggctgggggc tgg                                               23

<210> SEQ ID NO 53
<211> LENGTH: 23
<212> TYPE: DNA
<213> ORGANISM: Homo sapiens

<400> SEQUENCE: 53
ggaaggtggg tgctgggggc tgg                                          23

<210> SEQ ID NO 54
<211> LENGTH: 23
<212> TYPE: DNA
<213> ORGANISM: Homo sapiens

<400> SEQUENCE: 54
tggggctacg tcctgggggc cag                                          23

<210> SEQ ID NO 55
<211> LENGTH: 23
<212> TYPE: DNA
<213> ORGANISM: Homo sapiens

<400> SEQUENCE: 55
tgagtgtggg tgctgggggc cag                                          23

<210> SEQ ID NO 56
<211> LENGTH: 23
<212> TYPE: DNA
<213> ORGANISM: Homo sapiens

<400> SEQUENCE: 56
ggaggttggg ggctgggggc tgg                                          23

<210> SEQ ID NO 57
<211> LENGTH: 23
<212> TYPE: DNA
<213> ORGANISM: Homo sapiens

<400> SEQUENCE: 57
ggtgagtgag tgctgggggc agg                                          23

<210> SEQ ID NO 58
<211> LENGTH: 23
<212> TYPE: DNA
<213> ORGANISM: Homo sapiens

<400> SEQUENCE: 58
aggggctggg ggctgggggc tgg                                          23

<210> SEQ ID NO 59
<211> LENGTH: 23
<212> TYPE: DNA
<213> ORGANISM: Homo sapiens

<400> SEQUENCE: 59
tggggctggg cgctgggggc cag                                          23

<210> SEQ ID NO 60
<211> LENGTH: 23
<212> TYPE: DNA
<213> ORGANISM: Homo sapiens

<400> SEQUENCE: 60
gagggccgcg tcctgggggc ggg                                          23

<210> SEQ ID NO 61
<211> LENGTH: 41
<212> TYPE: DNA
<213> ORGANISM: Homo sapiens

<400> SEQUENCE: 61
ctggcagccc tggaccccaa ggccccgttg gccccctgg a                                41

<210> SEQ ID NO 62
<211> LENGTH: 36
<212> TYPE: DNA
<213> ORGANISM: artificial
<220> FEATURE:
<223> OTHER INFORMATION: cDNA

<400> SEQUENCE: 62
tggcagccct ggaccccaag gccccgttgg cccccc                                    36

<210> SEQ ID NO 63
<211> LENGTH: 3830
<212> TYPE: DNA
<213> ORGANISM: artificial
<220> FEATURE:
<223> OTHER INFORMATION: polynucleotide

<400> SEQUENCE: 63
tcccagaggc agggaagccc tctgccttgt cgctgccctt gtgcctggaa ttgggctctg          60
tgaagctctg aggggccatt tctctgcctc actgttccac ccccaataac acttgggggt         120
cagtggggta ggcgacccct tgttgatggg gtgaggcccc tccagcaaac cagggggcctt         180 ggggggaggggt cccttcctgt cctgacctct tcacctcctc agggcttccc tggagcagat         240
gggcgtccag gcagccctgg ccgcgccggg aatcctggga cccctggagc ccctggccta         300
aaggtgagca agccttgtcc tgcaggtcag ggtgggcgct gcctgagtgg gtggggtggc         360
tccgactgtt ctgcctctgg cctccatttg cagggctctc cagggttgcc tggccctcgt         420
ggggacccgg taaggtgcct tcccttcttt gctctctaag tgtcttccca gggttcttcc         480
acagggtggg agcctggggt ggtggtgcag tgcccacgtt gacattcgcc tgagcccaag         540 caccacctc tgctctgttt cgtcctcagg gagagcgagg acctcgaggc ccaaaggggg         600
agccggtagg tgaaggggga agggaggcgg ccggatgtc caggaggga gcaggactgc         660 cccacaccag accctgtgca gggcctaagg cgcgaatagg aatagctgga catgtctagg         720
ggcttcttcc agctcaaggc ccccatagcc tgaatcctgc ccactgctct ctgtccttac         780 aggggggctcc cggacaagtc atcgaggtg aaggacctgg gcttcctggg cggaaagggg         840
accctggacc atcggtaagt gcagggtatg tggaggcaag tgatgtgtag tggggggacc         900
aacacgaggg gggcgagagt gaggtctgtg gggttgcacc ttatactttg tctcctccat         960
cagggccccc ctgacctcg tggaccactg ggggaccccag gaccccgtgg cccccaggg        1020 cttcctggaa cagccatgaa ggtgacagcc tcatgagtgc catgtgatgc agagacctgg        1080
tgaccccatt tgaacccaca taaccccctgc cagttactct ggcccttgtg accctttgat        1140
tacccccatc ctcaccatga cgcctcagtt ctcccaaaat ccttgaaatc caattggacc        1200
ccatgaccct catcactcct ggtatctttg ggagtgaggt gtgcccagg gtcatggggt        1260 cgtcatctgt tttctagggt gacaaaggcg atcgtgggga gcgggtaagt gagggacagg        1320
ttgtgctagg ggtggcttgg agtctgattc ccctgttcat tccctgacct gctgttctct        1380
cccagggtcc ccctggacca ggtgagggcg gtatcgcccc aggagagcct gggctgccgg        1440
tgaggggcct tgaggctctg ctggggggccc tgctcagggg tgtgggtctc tcctgggca        1500 gtggttgggt gctgggcttc atagttcttg ctcatatttt tactcacttc ttcctagggt        1560
cttcctggca gccctggacc ccaaggcccc gttggccccc ctggaaagaa aggagaaaaa        1620

```
gtaggaaggc tgacttgatg atgtcccagt tctggggtgg gaggctgcgt gctgggggca    1680
gcctcccttc ggtcttccca cccgtgtgtt tctccttcag ggtgactctg aggatggtgc    1740
ccctggcctg cctggccaac ctgggtctcc ggtgagcag gtgagtggag gggccaggga     1800
ttctgaatat ggtgggcaca gctccagccc ctacctcaat catcaaccac tgctccatcc    1860
tcatgcccaa acccaaatct ctgaaccccc aaattcatcc cttccagggc ccacgggac     1920 ctcctggagc tattggcccc aaagtgagta ccagttgggg gattcaggtg tgaggggtgc    1980
tactctgggc tccccatggt gttaggggag gctggaagat aaggagataa gagttccctc    2040
caggtcagag gtcgtggttt tggagggggt ggttggagtt tggaccccct tgtctggggt    2100
ttgacgttca agccccgcca ccaaccctct ctctctctgt ctttctctca ccctctctct    2160
tcagggtgac cggggctttc cagggcccct gggtgaggct ggagagaagg taagtgcaac    2220 ctgggggtg ccaagggccc tggaggatct gggcccaact cagctctgac ctcttctttt     2280
ccatcagggc gaacgtggac ccccaggccc agcgggatcc cgggtaaacc cactggctgc    2340
aatgctcata ccagctgacc tggctgtgcc ctttctggtt ctgacttctt gcccttgacc    2400
cctgctaccc ctgctcctca cccctcctca atgaccactt atccctgctg atacaggctc    2460
taaccctcag ccccagggac ctggctttga acctctgacc ctgctgaact gaccttgatt    2520
ttcactgacc tggtctctgt tctcctgcca agtcttaccc ctgccaacct aaatcccaat    2580
cttccctgac ccctctccag ccccaccccc agcctctagc cctgtctgtc catatccccc    2640
gtccccaccc acctgcacag ctcttcccctt cctctcctcc aggggctgcc aggggttgct    2700
ggacgtcctg gagccaaggg tcctgaagtg agtctgtgac tgtggtggga ccaggagtgg    2760 gactttgtg tgtccctccc ctttcccttc ccctcctggg ctcacacttt ctctacattc     2820
aggggccacc aggacccact ggccgccaag gagagaaggt gggtcctcgg ctgggggtgg    2880
cactgtctgg tactagggat gtggcagatg ggacactggg attttgggct cctaggtgac    2940
tccctgacct gtccctgctc ctatcctctc tccacagggg gagcctggtc gccctgggga    3000
ccctgcagtg gtggtgagtg acgggaggat ggcgctctga gcacagcaca gcccttgagc    3060
agtgaccctc ctatagaaca ctatctgggc tgtgattcca cagtgctggg cccgtgagca    3120
ggctgggagc tctgcggctc tccttctgct agaacctgcc cccagactct tggctatgat    3180
cctgtgaccc caagaccgcc atgcaggtca tgagctcttt gtgtcagtcc attttgtata    3240
accccttccc tgctgtcagc ggtgactctg tgacttctgg gcggggactg agctgtatga    3300
cttccaattc catgtgacct ccattccaat gaagactttg atcatacaac cccaaggcag    3360
ggccaagctg tatctgtcct gtttgttttc agggacctgc tgttgctgga cccaaaggag    3420
aaaaggtaag cctggtatgg ggcaagggga ggtttctaca gggttgaggt ctaggtcata    3480
gggcctatct atgggacttg ggggtcaca ggacttgctg ggtcaggggg ttaactggag     3540
cctgggacta gcactgatgg tctttgtcac ctccagggag atgtggggcc cgctgggccc    3600
agaggagcta ccggagtcca aggggaacgg gtaagtgaag cgaagtgttt agggggcagt    3660
tggtgaaggt tgtcttcctg acttcttatc cttccatcca cagggcccac ccggcttggt    3720
tcttcctgga gaccctggcc ccaagggaga ccctggagac cgggtgaatc aatgtgggaa    3780
tggggagtgt gacagaggga gatgaggtgg tgggaccctg actaagtcct                3830
```

METHOD FOR CORRECTING A GENETIC SEQUENCE

CROSS-REFERENCE TO RELATED APPLICATION

This application claims priority to U.S. Provisional Patent Application No. 62/425,405, filed Nov. 22, 2016, which is incorporated herein by reference in its entirety.

GOVERNMENT FUNDING

This invention was made with government support under AR063070 and CA065493 awarded by National Institutes of Health. The government has certain rights in the invention.

SEQUENCE LISTING

This application contains a Sequence Listing electronically submitted via EFS-Web to the United States Patent and Trademark Office as an ASCII text file entitled "11005630101SequenceListing_ST25.txt" having a size of 16 kilobytes and created on Dec. 11, 2017. The information contained in the Sequence Listing is incorporated by reference herein.

BACKGROUND

Recessive dystrophic epidermolysis bullosa (RDEB) is a severe, monogenic disorder caused by mutations to the type VII collagen gene (COL7A1) on chromosome 3. The mutations deactivate production of a structural protein, type VII collagen protein (C7), that affects skin integrity. The loss of C7 at the dermal-epidermal junction compromises the integrity of the attachment of the epidermis to the dermis, resulting in severe blistering, fibrosis, and a predisposition to squamous cell carcinoma. Non-cutaneous manifestations, including corneal and esophageal lesions, further contribute to a pathogenic state leading to a multi-decade decrease in life expectancy.

Existing treatments for RDEB include palliative bandaging of active wounds and pain management, as well as allogeneic and autologous cellular therapy. Palliation is non-curative, and cellular therapy can include localized injection of type VII collagen-expressing cells and/or systemic infusion of hematopoietic stem/progenitor cells (HSPCs) that repopulate the host with donor-derived cells. Keratinocytes and fibroblasts represent the major C7 producing cells of the skin; however, their poor in vitro proliferative and expansion properties as primary cells limit their therapeutic potential and impact. Mesenchymal stromal/stem cells (MSCs) have been used as a supportive therapy and possess wound migratory potential and the ability to actively participate in, as well as to orchestrate, healing. But, similar to other primary cells primary, bone marrow-derived MSCs can senesce and lose their beneficial properties with in vitro expansion.

To mediate systemic effects, allogeneic hematopoietic cell transplant (HCT) has been employed. HCT has resulted in significant, but neither uniform nor complete, outcomes. For each modality, the use of allogeneic cells limits efficacy. Locally injected cells appear to persist transiently, likely due to immune clearance, necessitating repeated injections that are limiting in terms of the difficulty in long-term culture/maintenance, surface area able to be treated, and availability of allogeneic cells that can be obtained, archived, and expanded for subsequent injections. HCT can result in graft-versus-host disease that can cause severe side effects.

SUMMARY OF THE INVENTION

This disclosure describes methods that include cellular reprogramming and precision gene correction, providing a platform for producing autologous cell-types for regenerative medicine. In one aspect, this disclosure describes methods of gene correction, methods of generating induced pluripotent stem cells (iPSCs), and methods of deriving multi-lineage cell types with therapeutic value. In some embodiments, the gene correction affects the expression and/or function of the functional type VII collagen protein (C7).

In one aspect, this disclosure describes a method including introducing into a cell that includes a genomic sequence in need of editing: a donor template polynucleotide that includes a polynucleotide that encodes an edited version of the genomic sequence; a polynucleotide that encodes a clustered regularly interspaced short palindromic repeat associated (Cas) nuclease or nickase; and a guide RNA (gRNA); allowing the nuclease to cut at least one strand of the genomic sequence; and allowing the edited version of the genomic sequence to replace the genomic sequence in need of editing to produce a cell comprising a donor sequence.

In some embodiments, the cell that includes a genomic sequence in need of editing is a fibroblast. In some embodiments, the genomic sequence in need of editing encodes a portion of the type VII collagen gene (COL7A1). In some embodiments, the Cas nuclease or nickase comprises at least a portion of Cas9. In some embodiments, the donor template polynucleotide comprises a drug resistance gene.

In some embodiments, the gRNA can include at least one of:

```
                                    (SEQ ID NO: 43)
    GTGCTGGGCTTCATAGTTCTTGG, (SEQ ID NO: 44)
    GGAGGCTGCGTGCTGGGGGCAGG,
    and (SEQ ID NO: 45)
    GCCTTGGGGTCCAGGGCTTCCGG.
```

In some embodiments, the method further includes generating a clone from the cell comprising a donor sequence. In some embodiments, the method further includes reprogramming a cell comprising a donor sequence to obtain an induced pluripotent stem cell (iPSC). In some embodiments, reprogramming the cell comprises Sendai virus-based reprogramming.

In some embodiments, the method further includes differentiation of an iPSC to form an iPSC-derived cell. In some embodiments, differentiation of the iPSC includes differentiation to at least one of a keratinocyte, a mesenchymal stem cell (MSCs), and a hematopoietic progenitor cell.

In some embodiments, the method includes two-dimensional culture of an iPSC in media comprising at least one of retinoic acid and bone morphogenic protein 4 (BMP-4).

In some embodiments, the method includes exposing an iPSC to media comprising at least one of platelet-derived growth factor (PDGF)-AB, basic fibroblast growth factor (bFGF), and epidermal growth factor (EGF).

In some embodiments, the method includes exposing an iPSC to media comprising a Rho-associated protein kinase (ROCK) inhibitor.

In some embodiments, the method includes embryoid body (EB) formation. In some embodiments, EB formation comprises exposing an iPSC to a serum free media.

In some embodiments, the method includes inhibiting at least one of Activin/Nodal and GS3Kβ.

In some embodiments, the method includes co-culture of, for example, an iPSC, with vascular stroma.

In some embodiments, the method further includes isolating a cell that comprises a genomic sequence in need of editing from a subject. In some embodiments, the method further includes introducing the cell including a donor sequence and/or an iPSC-derived cell including a donor sequence into the subject.

As used herein, the term "animal" refers to living multicellular vertebrate organisms, a category that includes, for example, mammals and birds. The term "mammal" includes both human and non-human mammals. Exemplary mammals include humans, non-human primates, dogs, cats, sheep, mice, horses, and cows. In some embodiments, the mammal is a human.

The terms "subject," "host," "individual," and "patient" are as used interchangeably herein to refer to a human or a veterinary subject such as, for example, a human, a non-human primate, a dog, a cat, a sheep, a mouse, a horse, or a cow. In some embodiments, the subject is a human.

As used herein, the terms "nucleic acid sequence," "oligonucleotide," and "polynucleotide" are used interchangeably to refer to a polymeric form of nucleotides of any length, either ribonucleotides or deoxyribonucleotides. Thus, this term includes, but is not limited to, single-stranded, double-stranded, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. A polynucleotide can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can include modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

The term "encode," as it is applied to nucleic acid sequences, refers to a polynucleotide that is said to "encode" a polypeptide if, in its native state or when manipulated by methods well known to those skilled in the art, can be transcribed to produce an mRNA that may be translated to produce the polypeptide and/or a fragment thereof. The antisense strand is the complement of such a nucleic acid, and the encoding sequence can be deduced therefrom.

As used herein, the term "vector" refers to a nucleic acid construct designed for transfer between different hosts, including but not limited to a plasmid, a virus, a cosmid, a phage, a bacterial artificial chromosome (BAC), a yeast artificial chromosome (YAC), etc. In some embodiments, a plasmid vector may be prepared from a commercially available vector. In other embodiments, a viral vector may be produced from a baculovirus, a retrovirus, an adenovirus, an AAV, etc., according to techniques known in the art.

An "effective amount" or "efficacious amount" refers to the amount of an agent, or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

Unless otherwise intended, when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, a reference antibody, a reference polypeptide, or a reference nucleic acid having at least minimal homology while still maintaining desired structure or functionality. Unless specifically recited herein, it is contemplated that any polynucleotide, any polypeptide, or any protein mentioned herein also includes equivalents thereof. For example, an equivalent can exhibit at least about 70% homology or identity, or at least 80% homology or identity, at least about 85% homology or identity, at least about 90% homology or identity, at least about 95% homology or identity, or 98% percent homology or identity and exhibit substantially equivalent biological activity to the reference protein, reference polypeptide, or reference nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may include two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. Stringent hybridization conditions can employ equivalents of SSC using other buffer systems.

The term "isolated" as used herein refers to molecules or biologicals or cellular materials being substantially free from other materials. In one aspect, the term "isolated" refers to nucleic acid, such as DNA or RNA, or protein or polypeptide (including, for example, an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments that are not naturally occurring as fragments and would not be found in the natural state. The term "isolated" is also used herein to refer to polypeptides that are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, a "pluripotent cell" also termed a "stem cell" defines a cell that can give rise to at least two distinct (genotypically and/or phenotypically) differentiated progeny cells and is less differentiated than the progeny cells. In another aspect, a "pluripotent cell" includes an induced pluripotent stem cell (iPSC), which is an artificially derived stem cell from a non-pluripotent cell, typically an adult somatic cell, produced by inducing expression of one or more stem cell specific genes. Such stem cell specific genes include, but are not limited to, the family of octamer transcription factors, i.e., Oct-3/4; the family of Sox genes, i.e., Sox1, Sox2, Sox3, Sox 15 and Sox 18; the family of Klf genes, i.e., Klf1, Klf2, Klf4 and Klf5; the family of Myc genes, i.e. c-myc and L-myc; the family of Nanog genes, i.e., OCT4, NANOG and REX1; or LIN28. Examples of iPSCs are described in Takahashi et al. *Cell* 131(5):861-872 (2007); Takahashi et al. *Cell* 126:663-76 (2006); Okita et al. *Nature* 448:260-262 (2007); Yu et al. *Science* 318(5858): 1917-20 (2007); and Nakagawa et al. *Nat. Biotechnol.* 26(1):101-6 (2008), Tolar et al. *J Invest Dermatology* 131 (4): 848-56 (2011). A "multi-lineage stem cell" or "multipotent stem cell" refers to a stem cell that reproduces itself and at least two further differentiated progeny cells from distinct developmental lineages. The lineages can be from the same germ layer (i.e., mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin). A "stem cell" may be categorized as somatic (adult) or embryonic. A somatic stem cell is an undifferentiated cell found in a differentiated tissue that can renew itself (i.e., is clonal) and, with certain limitations, can differentiate to yield each of the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell, including, for example, a stem cell. Certain stem cells may be CD34+ stem cells. CD34 is a cell surface marker. An amino acid sequence for CD34 and a polynucleotide that encodes CD34 is reported under GenBank number M81104 (X60172).

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal or ectodermal or endodermal lineage" defines a cell that becomes committed to a specific mesodermal or ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

The terms "protein", "peptide," and "polypeptide" are used interchangeably and in their broadest sense to refer to a compound of two or more subunit amino acids, amino acid analogs, or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids in a protein peptide. As used herein the term "amino acid" refers to a natural amino acid, an unnatural amino acid, or a synthetic amino acid, including glycine and both the D and L optical isomers, amino acid analogs, and peptidomimetics.

The term "expanded" refers to any proliferation or division of cells. A "cultured" cell is a cell that has been separated from its native environment and propagated under specific, pre-defined conditions. The term "culturing" refers to the in vitro propagation of cells or organisms on or in media of various kinds. The descendants of a cell grown in culture may not be completely identical (i.e., morphologically, genetically, or phenotypically) to the parent cell. The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type.

As used herein, "treating" or "treatment" of a condition in a subject refers to reducing, limiting progression, ameliorating, or resolving, to any extent, the symptoms or signs related to a condition. "Symptom" refers to any subjective evidence of disease or of a patient's condition. "Sign" or "clinical sign" refers to an objective physical finding relating to a particular condition capable of being found by one other than the patient. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject—e.g., to a subject "at risk" of developing the condition. A subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition.

The words "preferred" and "preferably" refer to embodiments of the invention that may afford certain benefits, under certain circumstances. However, other embodiments may also be preferred under the same or other circumstances. Furthermore, the recitation of one or more preferred embodiments does not imply that other embodiments are not useful, and is not intended to exclude other embodiments from the scope of the invention.

As used herein, the term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3(B-D) shows Trilineage differentiation. (C) Oil red-O staining demonstrating the ability of iPSC-derived MSCs to form adipose cells. (D) Alizarin red staining of osteogenic progeny. (E) Toluidine blue staining of chondrogenic cells from MSCs. (C), (D), and (E) are representative images of at least two different MSC pools and n=3-4 replicates.

FIG. 5. One exemplary embodiment of hematopoietic differentiation with vascular induction. (A) Exemplary experimental design. EBs formed over eight days (as shown in FIG. 4) were dissociated, sorted for CD34 cells, and then incubated on the VeraVec endothelial cell line expressing the E4ORF1 gene. (B) Multipotent hematopoietic progenitors. Upon vascular induction, small clusters of budding hemogenic cells (red triangles) were evident by light microscopy and gave rise to non-adherent hematopoietic progenitors. (C) FACS phenotype of iPSC CD34+ cells that underwent vascular induction. Day 8 CD34+ cells from EBs cultured on VeraVec cells for one week was analyzed by flow cytometry for CD34, 38, and 45. (D) Vascular induction CFU. CD34+ CD45+ cells isolated from the VeraVec feeder cells were cultured in methylcellulose, and representative colonies for CFU-GEMM (i and iii) and CFU-E (ii and iv) are shown. (E) CFU quantification. Three independent experiments were analyzed and quantified for the number of lineage-specific colonies formed for CD34+ cells derived+/−vascular induction. CFU-GEMM, colony-forming unit-granulocyte, erythrocyte, monocyte/macrophage, megakaryocyte; CFU-GM, colony-forming unit granulocyte-monocyte/macrophage; CFU-E, colony-forming unit erythroid; CFU-M, colony-forming unit monocyte/macrophage.

FIG. 6. One exemplary embodiment of CRISPR/Cas9 candidate testing. (A) COL7A1 gene sequence and CRISPR/Cas9 target sites (SEQ ID NO:42). The cytosine that is deleted in the RDEB-causing 4317elC genotype is shown in red. The protospacer adjacent motifs (PAM) for the CRISPR/Cas9 guide RNAs are underlined and proximity to the mutation is shown numerically in brackets. (B) CRISPR/Cas9 candidates. The three gene targets (SEQ ID NO:43, SEQ ID NO:44, and SEQ ID NO:45) with a space between the PAM sequences are shown. (C) CRISPR/Cas9 architecture. The gRNA (black line) recognizes a target site via Watson-Crick base pairing and complexes with the Cas9 nuclease protein (blue circles) that contain two domains (HNH andRuvC) that cleave a single strand of DNA. Inactivation of the HNH domain (indicated by red coloring) by a D10A substitution allows for a 'nicking' version of Cas9 that cuts one strand of DNA. (D) CRISPR/Cas9 gene delivery. The Cas9 nuclease or nickase was delivered on a plasmid under the control of the CMV promoter and bovine growth hormone polyadenylation signal (pA). The gRNA was expressed on a second plasmid from the U6 polIII promoter and a polyT transcriptional terminator. (E) Surveyor nuclease assay. CRISPR/Cas9-treated 293T cells were analyzed using Surveyor methodology by amplifying the COL7A1 region for which the gRNAs were designed. Modified (red box) and unmodified (green box) alleles in the amplicon pool were annealed and NHEJ-mediated indels led to imperfect pairing and cleavage of the DNA by Surveyor enzyme. (F) Polyacrylamide gel of Surveyor assay shown in (E).

FIG. 8. Exemplary morphology and karyotyping of patient-specific cells. (A) Morphology of gene-corrected fibroblasts. (B) Normal 46XX karyotype of the gene-corrected of (A). (C) Morphology of an iPSC colony derived from a gene corrected fibroblast (including defined and rounded borders). (D) Normal 46XX karyotypes of the reprogrammed iPSCs of (C).

DETAILED DESCRIPTION OF ILLUSTRATIVE EMBODIMENTS

Figure 1:
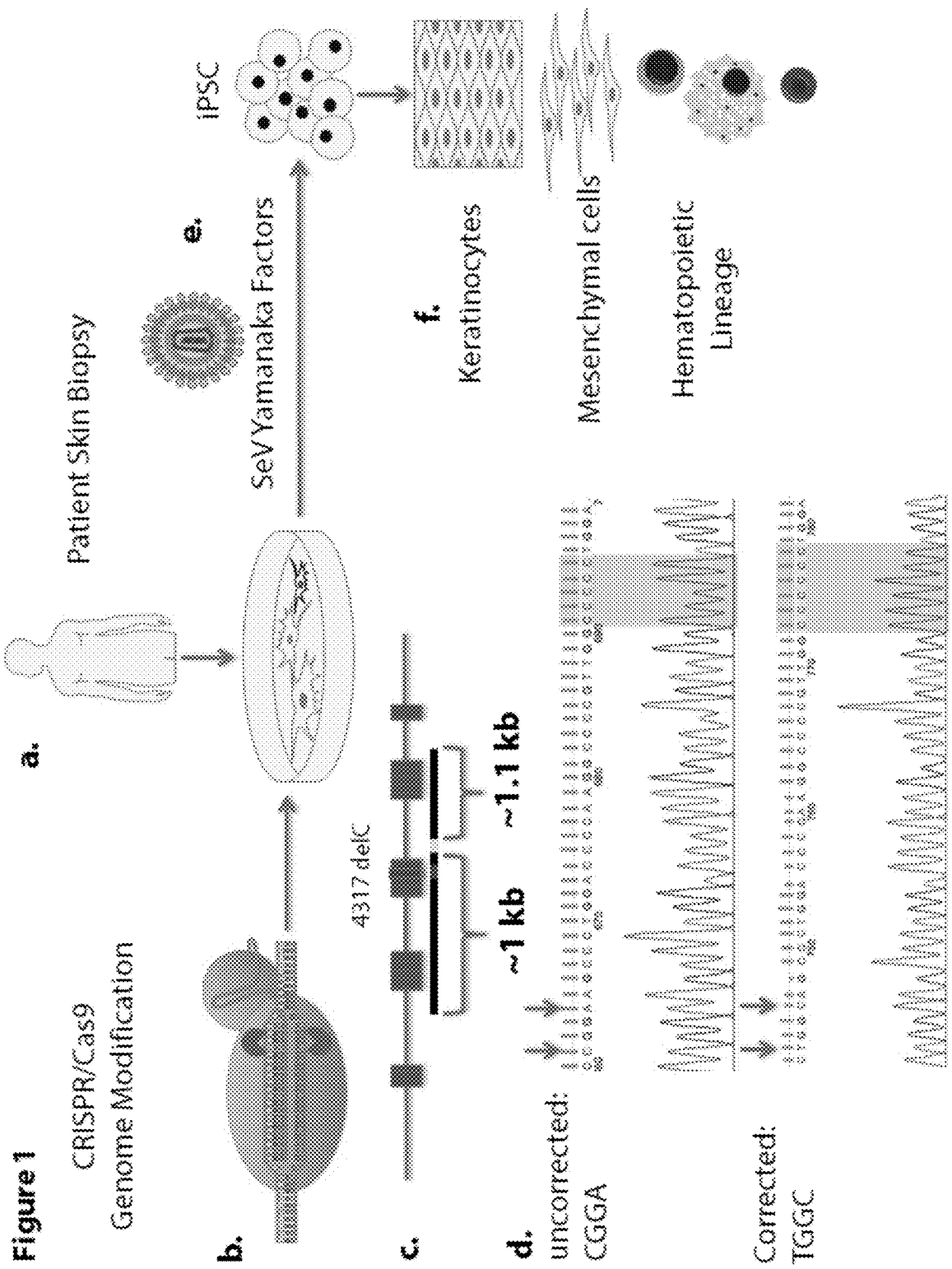
FIG. 1. An exemplary experimental schema for gene correction and cellular engineering. (A) A punch biopsy can be obtained for primary fibroblast cell derivation. (B) The CRISPR/Cas9 gene-editing platform can be employed for 4317delC COL7A1 gene correction. (C) COL7A1 locus and gene repair template. The 4317delC mutation is indicated with a red box. An exemplary donor template includes a plasmid containing ~1 kb of homology to the target sequence and flanked by a foxed PGK puromycin drug selection cassette (yellow box). A cytosine that restores proper genotype and two silent polymorphisms can be introduced into the donor arm and are indicated with a green box. (D) COL7A1 locus correction. Sanger sequence of uncorrected cells (SEQ ID NO:40) prior to treatment showing a sequence including a deletion of a single cytosine (delC) and an unmodified base sequence. Subsequent CRISPR/Cas9 mediated repair by the donor results in restoration of the deleted cytosine (shaded in blue) and incorporation of engineered marker SNPs (blue arrows) (SEQ ID NO:41). (E) The corrected fibroblasts can be reprogrammed to pluripotency using Sendai virus delivery of the reprogramming factors. (F) Induced pluripotent stem cells (iPSCs) can serve as a source for directed differentiation into keratinocytes, mesenchymal stem cells, and hematopoietic progenitors.

This disclosure describes methods of gene correction, methods of directly modifying primary HSPCs with long term engraftment potential and for generating induced pluripotent stem cells (iPSCs), and methods of deriving multi-lineage cell types from iPSCs. In some embodiments, the multi-lineage cell types preferably have therapeutic value. In some embodiments, this disclosure describes methods of gene correction in a primary HSPCs or a fibroblast; generation of an iPSC from the fibroblast; and generation of a keratinocyte, mesenchymal stem cell (MSC), and/or a hematopoietic cell from an iPSC. In some embodiments, the gene is preferably corrected using a CRISPR system. In some embodiments, the gene to be corrected affects the expression and/or function of the functional type VII collagen protein (C7).

TALENs for COL7A1 have been used for gene correction in fibroblasts and keratinocytes. This disclosure describes methods to fill two gaps in the current RDEB cellular and genome engineering procedures: i) integration-free derivation and subsequent feeder-free maintenance of iPSCs, and ii) the utilization of genetically corrected iPSCs for generation of multiple therapeutic cell types under defined conditions as proof of concept for multi-lineage cellular therapy (see, e.g., FIG. 1). In some embodiments, a gene correction strategy employs a CRISPR/Cas9 system that results in gene correction in fibroblasts. The fibroblasts can be of immediate value for localized C7 production. Furthermore, a Sendai reprogramming methodology can generate iPSCs that can be used for subsequent derivation of multi-lineage cell types with therapeutic value.

Two major platforms exist for facilitating gene correction: gene therapy and gene editing. Gene therapy for RDEB has centered primarily on lentiviral gene transfer of a copy of the COL7A1 cDNA, expression of which is governed by exogenous regulatory elements. While this strategy meets the need for autologous cellular engineering, there are significant hurdles to this approach. The large size of the cDNA can negatively impact viral titers making manufacturing, production, and efficient gene delivery rates suboptimal.

Further, the integrating properties of vectors capable of long-term gene expression represents a risk for insertional mutagenic-derived adverse events, a particular risk in RDEB patients that are at an increased risk for squamous cell carcinoma. Additionally, the artificial expression cassette components are not subject to the normal cellular gene regulatory environment, and the long-term effect of supraphysiological COL7A1 expression is unknown.

Gene editing for homology-directed repair (HDR)-based sequence correction at translational efficiency requires site-specific reagents that cleave the DNA helix. Zinc finger nucleases and transcription activator like effector nucleases (TALENs) function as dimeric proteins that co-localize at a target site and mediate a double-stranded DNA break. Meganucleases are a monomeric protein specified for a unique sequence utilizing a bacterial endonuclease as the engineering template. The clustered regularly interspaced palindromic repeats (CRISPR)/Cas9 reagent is a two-component system consisting of the Cas9 nuclease that conjugates with a small RNA transcript termed a guide RNA (gRNA). This complex interacts with a target sequence consisting of 15-20 nucleotides. Once a DNA break is generated, genome modification by HDR can occur using an exogenous donor DNA species as the repair template.

A CRISPR-based system can, in some embodiments, provide advantages over a TALEN-based strategy. Because of the robust targeting nature of, for example, CRISPR/Cas9, highly accurate HDR with minimal off target activity can be achieved. In addition, gene targeting can be developed more quickly. In a CRISPR-based system, gene targeting occurs via interaction of the gRNA with the nuclease (e.g., Cas9), and the gRNA can be rapidly assembled in less than one week using a small synthetic DNA sequence. In contrast, generation of a TALEN can require a month or more, including time to generate candidates, and can require specialized 'building blocks' of transcription activator-like (TAL) DNA binding repeats.

In one aspect, this disclosure describes genome editing in primary and patient-derived cells to create an autologous platform for multilineage engineering of therapeutic cell types.

For example, this disclosure describes, in one embodiment, the direct modification of primitive hematopoietic stem and progenitor cells. Because HCT is a current standard of care the use of modified HSPC has immediate therapeutic value. In another embodiment this disclosure describes the use of the CRISPR/Cas9 system to facilitate gene repair in patient derived fibroblast cells from an RDEB patient. Modification of cord blood CD34+ HSPCs and correction of COL7A1 fibroblasts was achieved. The fibroblasts were used as a renewable template for patient-specific induced pluripotent stem cell (iPSC) derivation. iPSCs were employed in a therapeutic engineering strategy to generate keratinocytes, MSCs, and hematopoietic cells.

Example 4 describes an exemplary gene correction strategy employing the CRISPR/Cas9 system that resulted in gene modification in HSPC and fibroblasts that are of immediate value for systemic and localized C7 production. Sendai reprogramming methodology was then employed to generate fibroblast-derived iPSCs that were used for subsequent derivation of multi-lineage cell types with therapeutic value.

Figure 7:
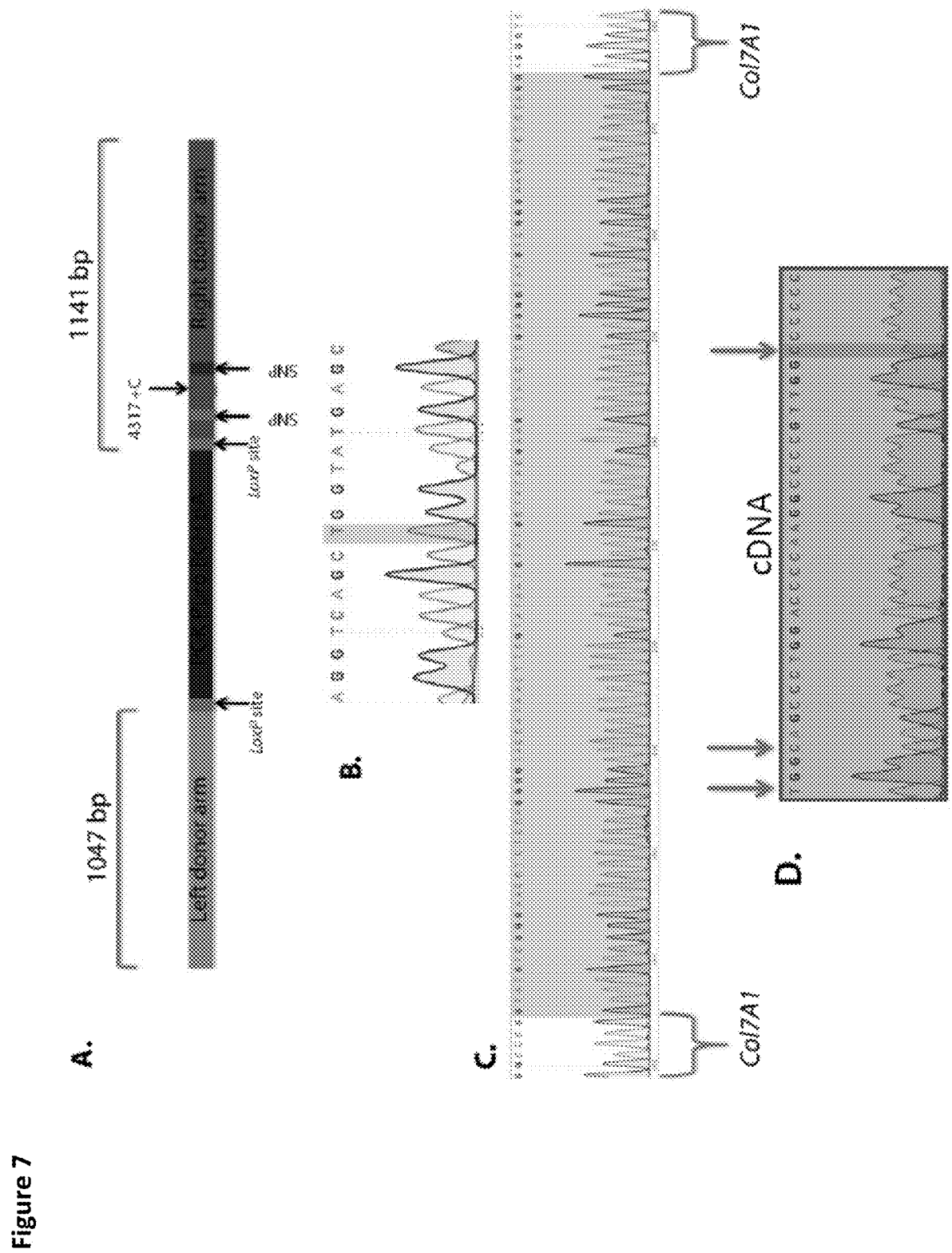
FIG. 7. One exemplary embodiment of homology-directed repair (HDR) donor and analysis. (A) Plasmid donor containing arms of homology termed left arm (1047 bp in length, orange box) and right arm (1141 bp in length, red box) flank a foxed (pink boxes) murine phosphoglycerate kinase 1 promoter driven puromycin resistance gene with a bovine growth hormone polyadenylation signal (blue box). The right donor arm contained two silent polymorphisms (SNP) and a sequence to restore the proper wild-type gene sequence at the 4317 delC locus. (B) Inside-out PCR sequencing. PCR primers to document HDR were employed with one inside the donor in the PGK sequence and the second outside the right donor arm. The blue highlighting shows the demarcation between donor sequence and endogenous COL7A1 locus sequence (SEQ ID NO:46). (C) Cre excision sequence (SEQ ID NO:47). iPSCs were subjected to cre mRNA electroporation were analyzed for the cre footprint (shaded region) contained to the intron. Included also were non-human CRISPR/Cas9 sequence as marker sequences. The endogenous COL7A1 sequences are shown with brackets at the termini. (D) cDNA analysis (SEQ ID NO:48). RNA from gene-corrected cells was analyzed for proper sequence documentation. A corrected base is highlighted in blue, and SNPs are indicated with arrows.
Figure 9:
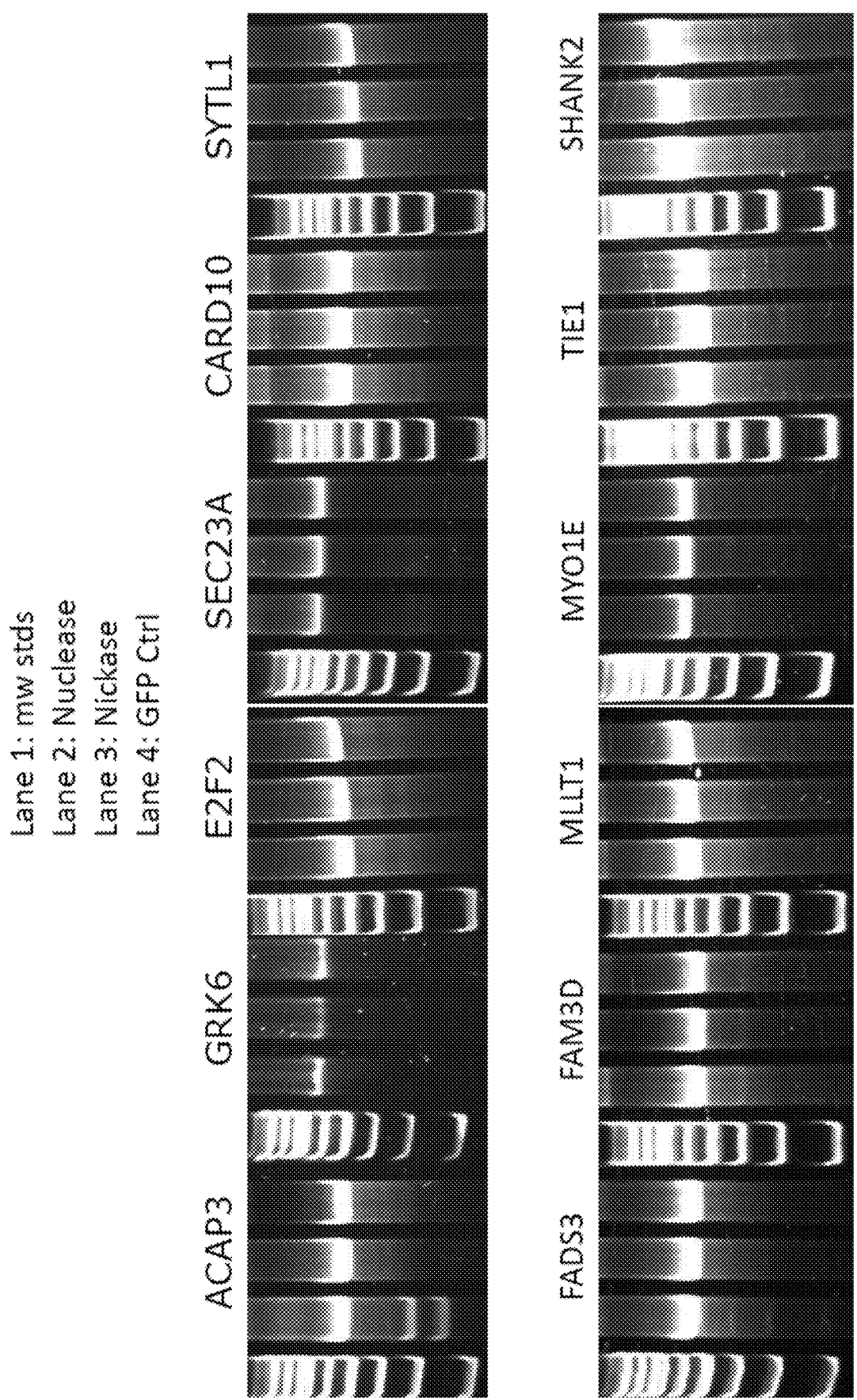
FIG. 9. Exemplary off-target analysis. HEK 293T cells were treated with the COL7A1 gRNA and the Cas9 nuclease, nickase, or a GFP transfection control plasmid. At 72 hours the predicted off-target loci were amplified by PCR and analyzed by the Surveyor method. Representative gel images with identical exposure rates are shown.

Three CRISPR/Cas9 targeting candidates were tested, with one employed for gene correction in comparative studies with the nuclease or nickase version of the *S. pyogenes* Cas9 (FIG. 6). Similar to previous observations, a lower overall rate of homology directed repair (HDR) was observed using the nickase (4/12 clones showing HDR vs. 8/12 for the nuclease) as observed; however, the preferential repair of DNA nicks by the homologous recombination (HR) pathway adds a further layer of specificity to the engineering process. This specificity is highlighted by the observation of an off-target event at the ACAP3 gene with the nuclease, but not nickase, version of Cas9 (Table 1, FIG. 9). The derivation of fibroblast clones was facilitated by a donor design strategy that included a puromycin cassette that was knocked into an adjacent intron for subsequent removal by cre-recombinase (FIG. 1, FIG. 7). This approach allowed a homogenous population of fibroblasts to be obtained by selection, as opposed to non-selection based strategies that have observed gene correction rates of <10%. Such selection is beneficial because the subsequent reprogramming process results in a sub-fraction of cells reprogrammed to pluripotency and, if the input is not uniform, extensive screening is mandated. Fibroblasts may be particularly useful because fibroblasts competent for C7 protein expression can be used for localized therapy in RDEB. Given the comparatively diminished proliferation capacity and rate of fibroblasts compared to iPSCs, gene correction in iPSCs was also attempted due to the fact that HDR occurs in late S and G2. Surprisingly, gene correction in this patient's iPSCs was not achieved, while 12 corrected fibroblast clones were obtained. One possible explanation for this is poor accessibility due to the chromatin status of iPSCs versus fibroblasts. Given that at the resolution of Western blotting C7 protein expression in iPSCs could not be detected (FIG. 12C), and the poor ability of nucleases to modify silent or repressed genes, the 4317 position of the COL7A1 locus may be refractory to gene modification as a result of chromatin state.

Figure 10:
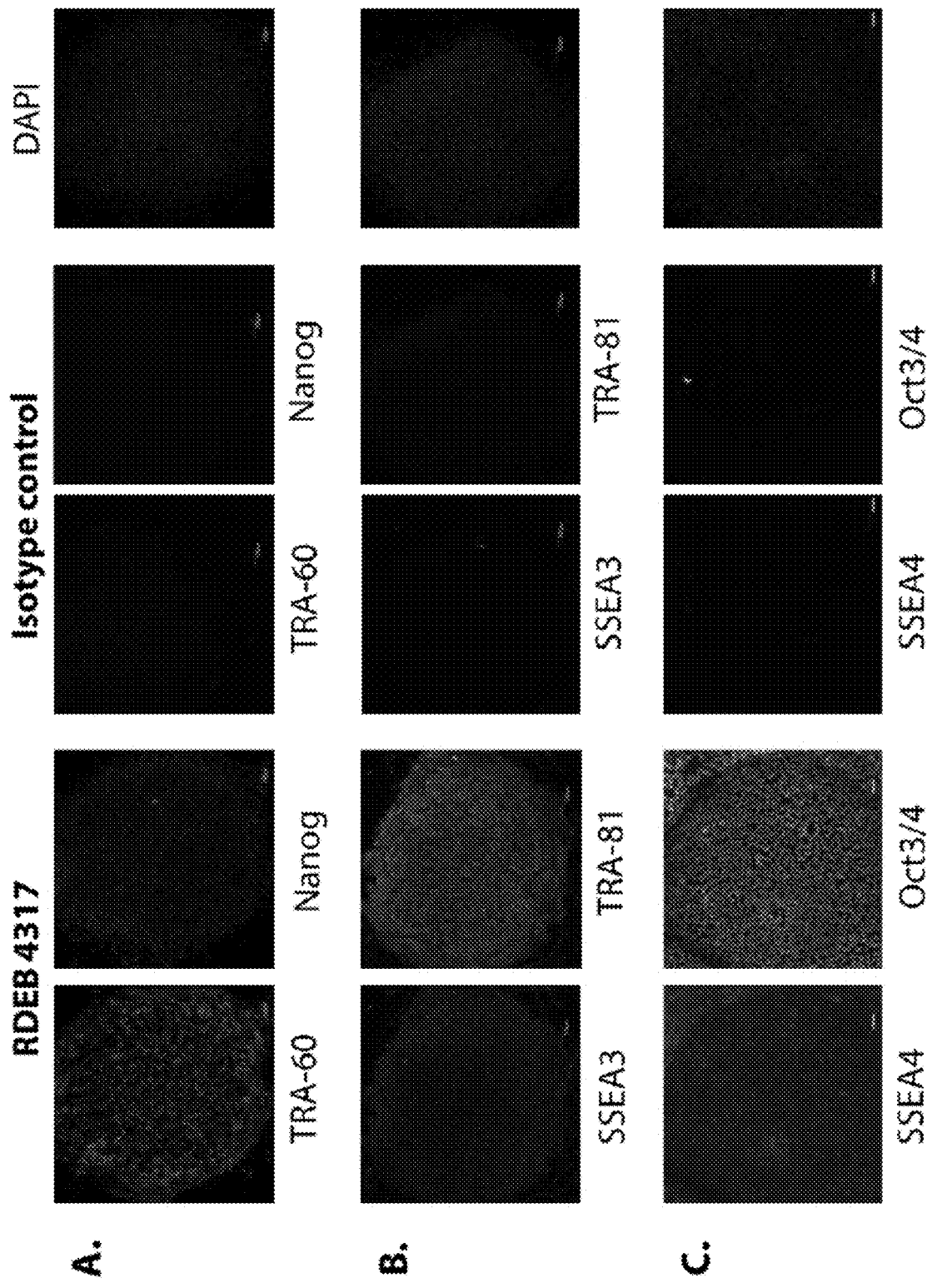
FIG. 10. An exemplary embodiment of iPSC phenotype after gene-correction and Sendai virus reprogramming. (A) iPSCs were analyzed for pluripotency-associated markers NANOG and TRA-60 by immunofluorescence. (B) iPSCs were analyzed for pluripotency-associated markers SSEA-3 and TRA-81 by immunofluorescence. (C) iPSCs were analyzed for pluripotency-associated markers SSEA-4 and OCT-3/4 by immunofluorescence.
Figure 11:
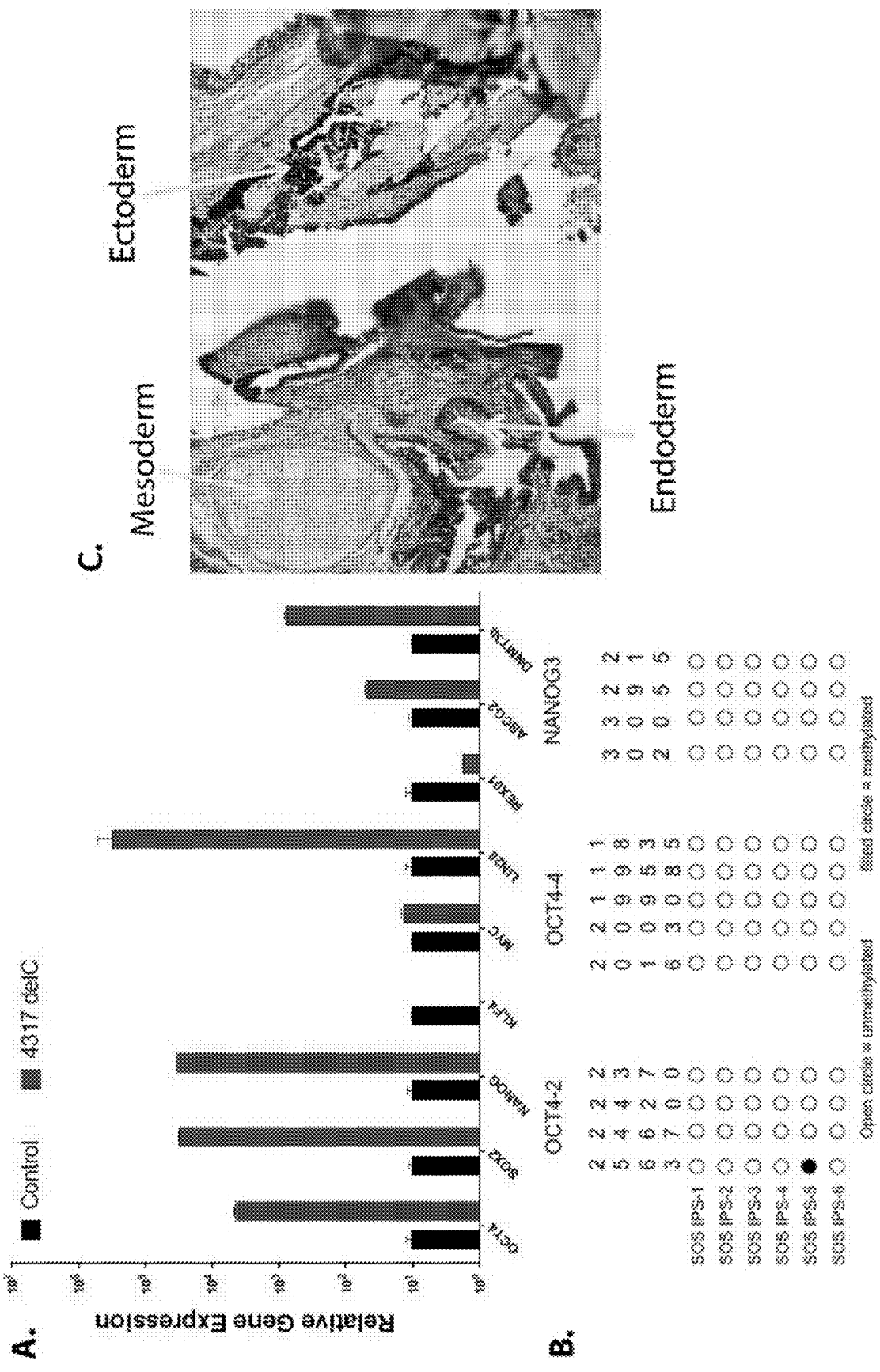
FIG. 11. One exemplary embodiment of iPSC gene and epigenome analysis. (A) TaqMan gene expression. qRT-PCR analysis of reprogramming associated genes was performed (n=3 replicates) in patient-derived fibroblasts and iPSCs. (B) Promoter methylation status. Sodium bisulfite treated DNA from patient-derived iPSCs (analyzed in triplicate with a representative image shown) was analyzed for the presence of methylated cytosines at the CpGislands in the OCT4 and NANOG gene promoters. (C) iPSC-derived teratoma. iPSCs were injected into the flank of NOD/scid IL2Rg null mice and excised. Shown is a representative image from 3-5 mice.

The Sendai virus reprogramming method is a non-integrating RNA virus platform that mediates robust reprogramming frequencies without retaining the reprogramming factors by virtue of natural loss by dilution as the cells divide (Fujie et al. *PLoS One* 9, e113052 (2014)). As such, the need for secondary factors (e.g., cre-recombinase) to remove the viral footprint is eliminated, as is the risk for adverse events associated with the random integration of viral vectors. Using this methodology, numerous clones were obtained and two were chosen (11-2 and 11-5) for iPSC quality assurance and control assessment. Each clone exhibited morphology consistent with pluripotency (i.e., discrete colonies with rounded edges), were karyotypically normal (FIG. 8), and expressed pluripotency-associated markers NANOG, TRA-60, -81, SSEA-3, -4, and OCT-3/4 (FIG. 10). Transcriptional profiling and promoter methylation analysis further confirmed successful reprogramming, and iPSC clones implanted into immune-deficient animals gave rise to teratomas consisting of tissues representative of all three germ layers (FIG. 11). These data demonstrate the successful reprogramming of CRISPR/Cas9 gene-corrected fibroblasts to iPSCs, which were subsequently maintained and propagated in feeder-free conditions and served as a renewable template for the generation of keratinocytes, mesenchymal stem cells (MSCs), and hematopoietic stem and progenitor cells (HPSCs).

Figure 2:
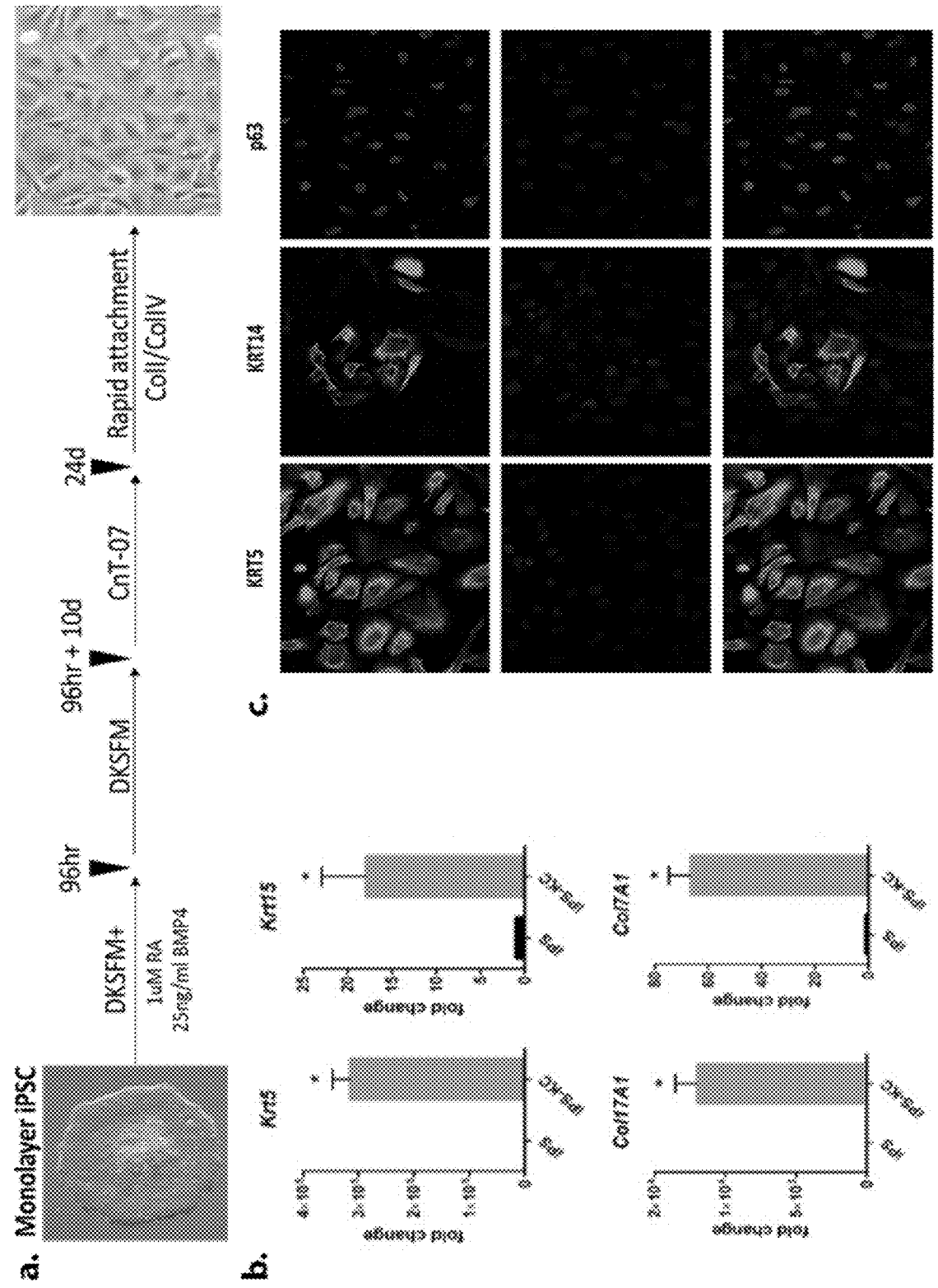
FIG. 2. One exemplary embodiment of keratinocyte generation. (A) Derivation schema. iPSC colonies in a 6-well plate were exposed to retinoic acid (RA) and bone morphogenic protein (BMP)-4 in defined keratinocyte serum-free media (DKSFM) with a transition to CnT-07 defined keratinocyte media. Keratinocytes were enriched by exploiting their ability to rapidly attach to collagen I and IV coated plates. (B) Keratinocyte gene expression analysis. TaqMan RT-qPCR was performed for keratin 5 and 15, COL17A1 and COL7A1 (three different experiments) and compared to parental iPSC. (C) Keratinocyte immunofluorescence. Gene-corrected, iPSC-derived cells were stained with anti-KRT5, KRT14 or p63 antibodies (top). Middle panel shows DAPI nuclear staining and bottom panel shows merged images that are representative of 3-4 independent experimental replicates.

Using defined conditions, epidermal cells with a morphology consistent with that of keratinocytes were derived, and these cells expressed the keratinocyte markers KRT5, KRT14, p63, COL17A1, and COL7A1 (FIG. 2). These iPSC-derived keratinocytes hold promise for localized application to chronic and/or severe wounds—either alone or in support of systemic therapy.

MSCs have shown promise as both a localized, and systemic therapeutic intervention in the setting of RDEB.

Figure 12:
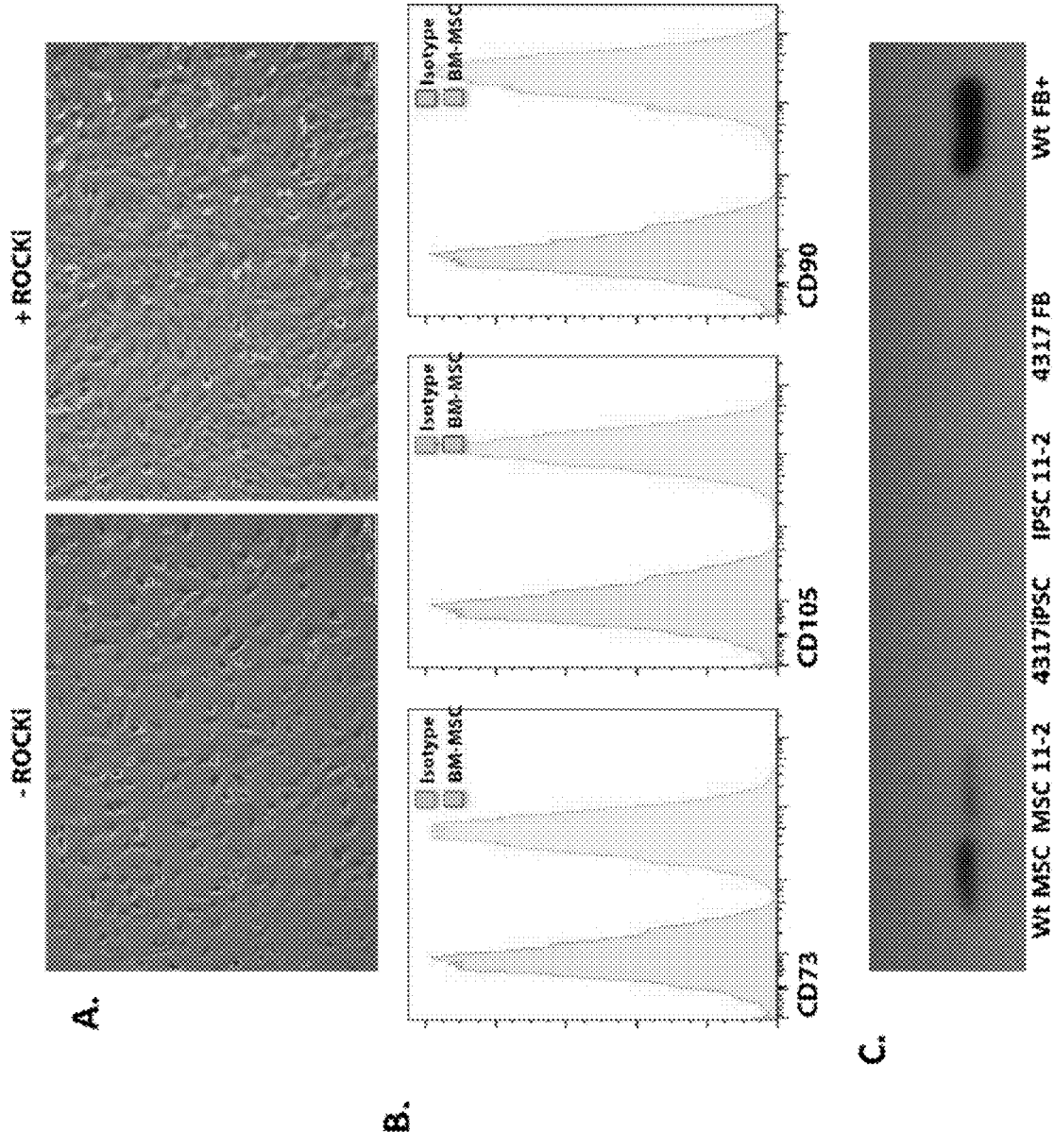
FIG. 12. One exemplary embodiment of MSC analysis. (A) ROCK inhibition enhances re-plating and survival of iPSC-MSCs. Images of iPSC-MSCs after the first passage with and without ROCK inhibition. (B) Bone marrow MSCs. MSCs were derived from a bone marrow aspirate from a human donor and assessed for cell surface expression of CD73, CD105, and CD90. (C) Cellular lysates were prepared and resolved on a gradient NuPAGE Gel (Invitrogen, Carlsbad, Calif.), transferred to a membrane and probed with a mouse anti-human collagen type VII antibody. A horseradish peroxidase conjugated secondary antibody was used for detection. From left to right the samples are: wild type MSC, gene corrected clone 11-2 MSC, uncorrected parental 4317 iPSC, gene corrected 11-2 iPSC, uncorrected 4317 fibroblasts and wild type fibroblasts.

However, genetic correction of MSCs has not been demonstrated, leading us to pursue in vitro production of MSCs from gene-corrected iPSCs. By exposing iPSCs to bFGF, PDGF, and EGF, and using ROCK inhibition during the early passages, robust MSC cultures were consistently produced (FIG. 12). These cells were morphologically identical to bone marrow-derived MSCs (FIG. 3A, FIG. 12), and were able to be expanded and propagated over multiple passages while retaining surface expression of CD73, CD105, and CD90, and the ability to undergo chondro-, osteo-, and adipo-genic differentiation in a manner identical to bone marrow-derived MSCs (FIG. 3(B)-(E), FIG. 12). From ~5×10$^6$ starting iPSCs, at least 1×10$^8$ iPSC-MSCs were routinely generated. Considering that a recent clinical trial using systemic delivery of MSCs for treatment of RDEB reported a dose of 1-3×10$^6$ per kg$^3$, this protocol is capable of generating clinically relevant yields of iPSC-MSCs.

Figure 4:
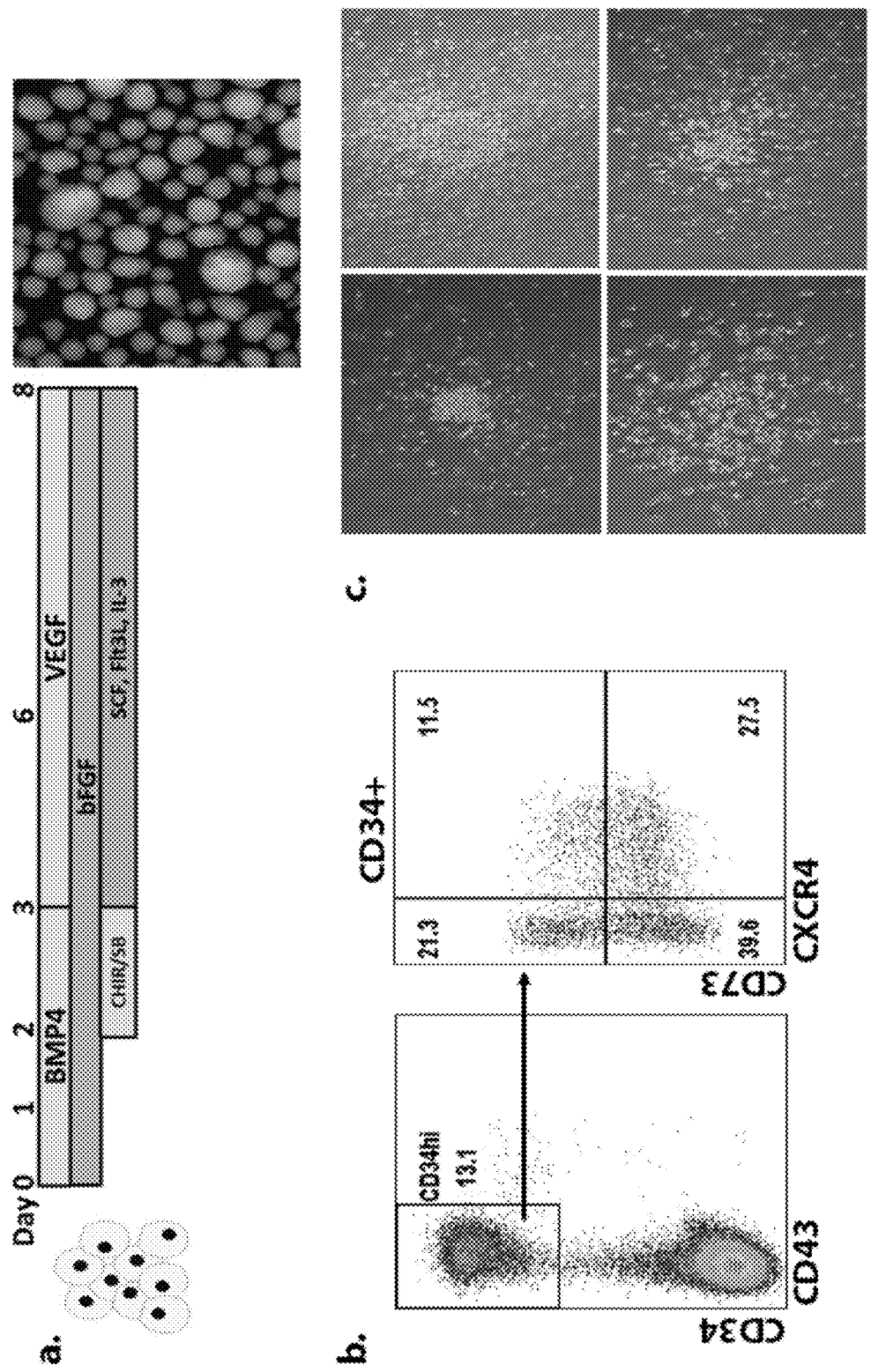
FIG. 4. One exemplary embodiment of hematopoietic differentiation. (A) Exemplary culture condition schema. Embryoid bodies were formed from iPSCs in the presence BMP4, VEGF, bFGF, CHIR99021, and SB431542, and hematopoietic cytokines (Flt3-ligand, SCF, and IL-3) over the course of eight days. A representative image of EBs is shown at right. (B) FACS phenotype of EB-derived CD34+ cells. Dissociated EBs were analyzed by FACS for expression of CD73 and CXCR4 in the CD34 high expressing population. (C) Methylcellulose colony-forming unit assay. CD34+ cells were embedded in methylcellulose, and an image of the dominating colony-forming unit granulocyte-monocyte/macrophage (CFU-GM) colony types are shown. The analyses/experiments are from at least four experimental replicate differentiation procedures.
Figure 14:
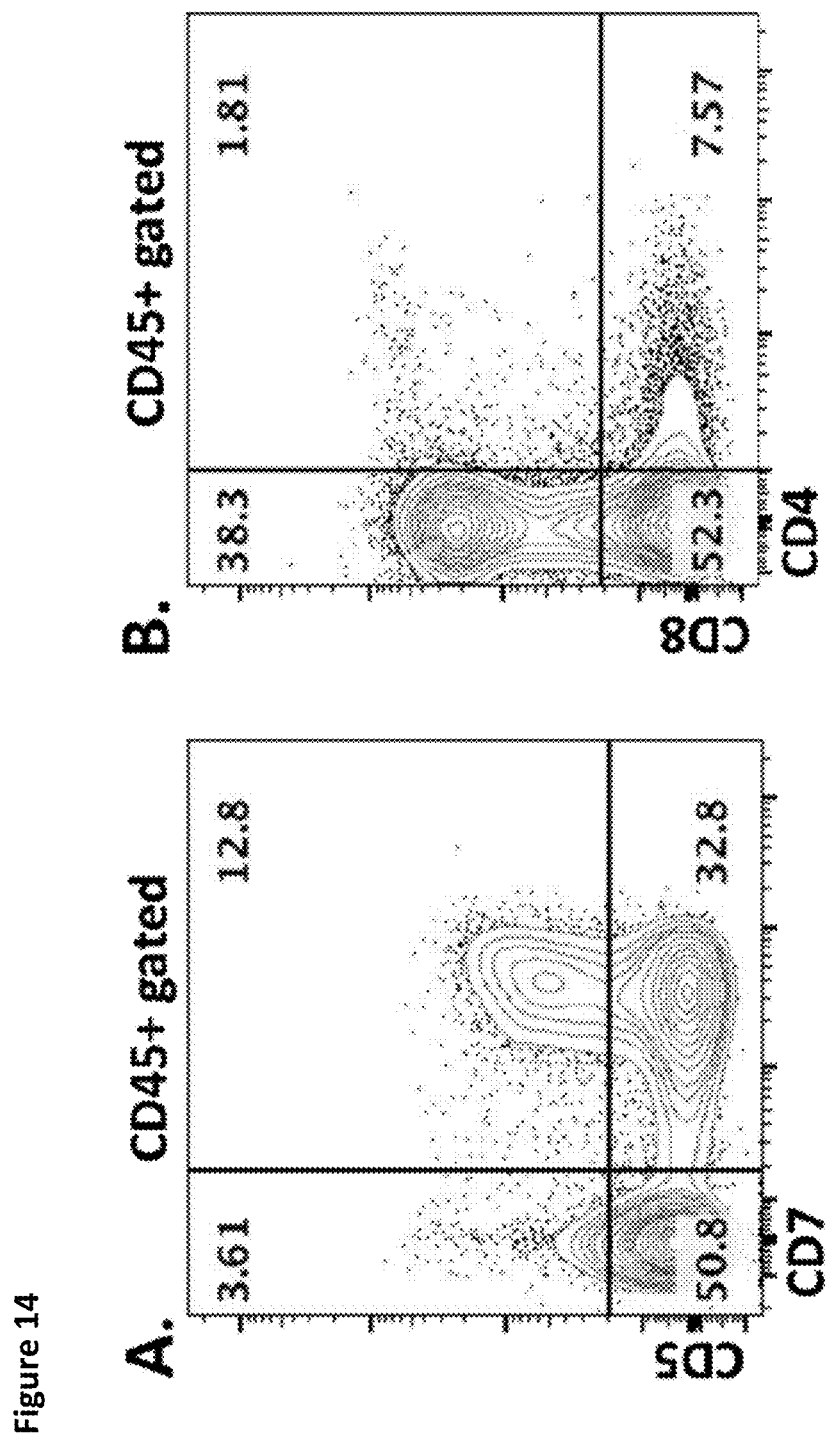
FIG. 14. Exemplary T-lineage differentiation. (A) Embryoid body-derived CD34+ cells were co-cultured with OP9-DLL4 and analyzed for early T-lineage specification by CD7 and CD5 expression. (B) Formation of CD4 and CD8+ fractions after extended OP9-DLL4 co-culture.

A challenging hurdle in stem cell biology remains the in vitro conversion of iPSCs to definitive HPSCs. Despite substantial effort, at the time of the invention, no robust, efficient, or clinically translatable method was available for converting iPSCs into HPSCs capable of long-term engraftment. This disclosure describes a more robust platform for producing definitive-type HPSCs including optimizing the basal media composition for robust production and growth of EBs from feeder-free iPSCs under fully defined conditions. This protocol centered on the stepwise induction of mesoderm with BMP-4 and bFGF followed by specification to hematopoiesis with vascular endothelial growth factor (VEGF), stem cell factor (SCF), interleukin (IL)-3, and Flt-3 ligand. Further steps include small molecule inhibition of the Activin/Nodal pathway with SB431542 and augmentation of the Wnt pathway via inhibition of GS3Kβ with CHIR99021 to drive definitive hematopoiesis (FIG. 4, FIG. 5, FIG. 14). Without wishing to be bound by theory, it is believed that the culture conditions and modulation of the primitive and definitive fate determinant modulators with CHIR99021 and SB431542 biases the cells away from primitive hematopoiesis and promotes definitive hematopoietic commitment. However, even though EB-derived CD34+ hemogenic precursors were definitive in nature as evidenced by their capacity for T-lineage differentiation, given the appropriate micro environmental cues, their intrinsic capacity for multilineage hematopoietic differentiation was limited in CFU assays (FIG. 4). A vascular induction technique aimed at recapitulating the complicated embryonic hematopoietic niche environment was employed ex vivo, to determine whether the instructive cues provided by the E4ORF1 transformed endothelial cells would promote maturation and expansion of EB-derived CD34+ cells to multilineage hematopoietic progenitors. In contrast to the data observed when EBs were used without vascular induction, the inclusion of the co-culture system resulted in the substantial increase of both progenitor frequency and multilineage capacity (FIG. 4, FIG. 5). These data outline a robust, reproducible strategy for the in vitro production of multilineage definitive HPSCs from iPSCs.

In conjunction with corresponding data showing the ability to correct RDEB-causing mutations and employ an engineering strategy that maximizes the potential of iPSCs for therapeutic cell generation, these results hold great promise for RDEB and other maladies that may benefit from regenerative medicine.

Figure 15:
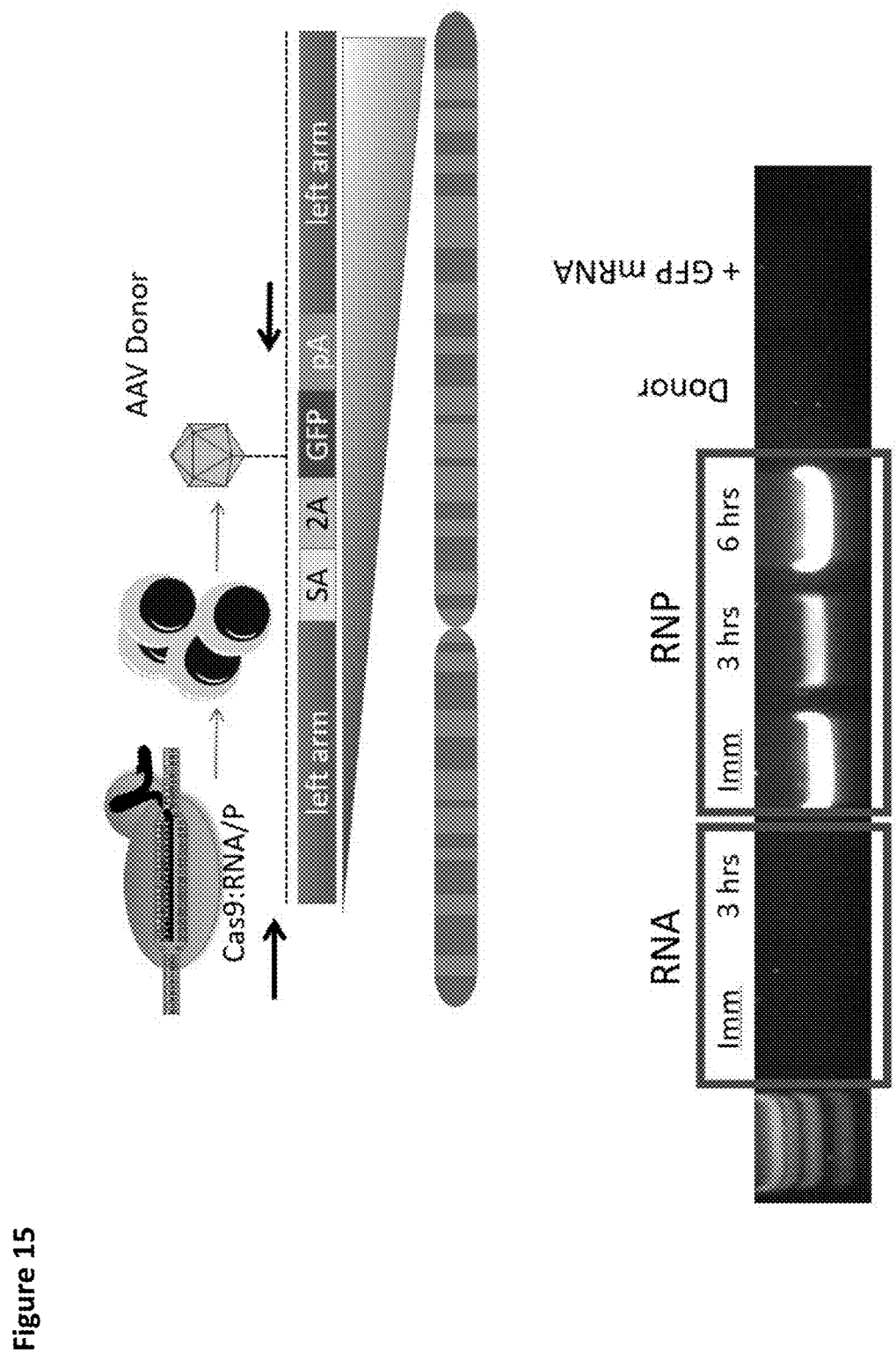
FIG. 15. Cas9 delivery optimization for human hematopoietic stem and progenitor cell gene editing. Cas9 RNA or RNP was delivered to cord blood obtained CD34 cells followed by a homologous recombination donor specific for the AAVS1 locus on chromosome 19. The donor contains homologous arms to the AAVS1 target site (left and right arms), a splice acceptor (SA), 2a peptide sequence, a GFP gene, and a polyadenylation signal (pA). The donor sequence was packaged in adeno-associated virus serotype-6 particles (AAV-6). Following electroporation, the AAVS1 targeting donor was added as AAV-6 particles at an MOI of $1\times10^5$ immediately (imm), three or six hours post electroporation. At 48 hours post gene transfer genomic DNA was screened for HR using an inside out PCR (arrows at top).
Figure 16:
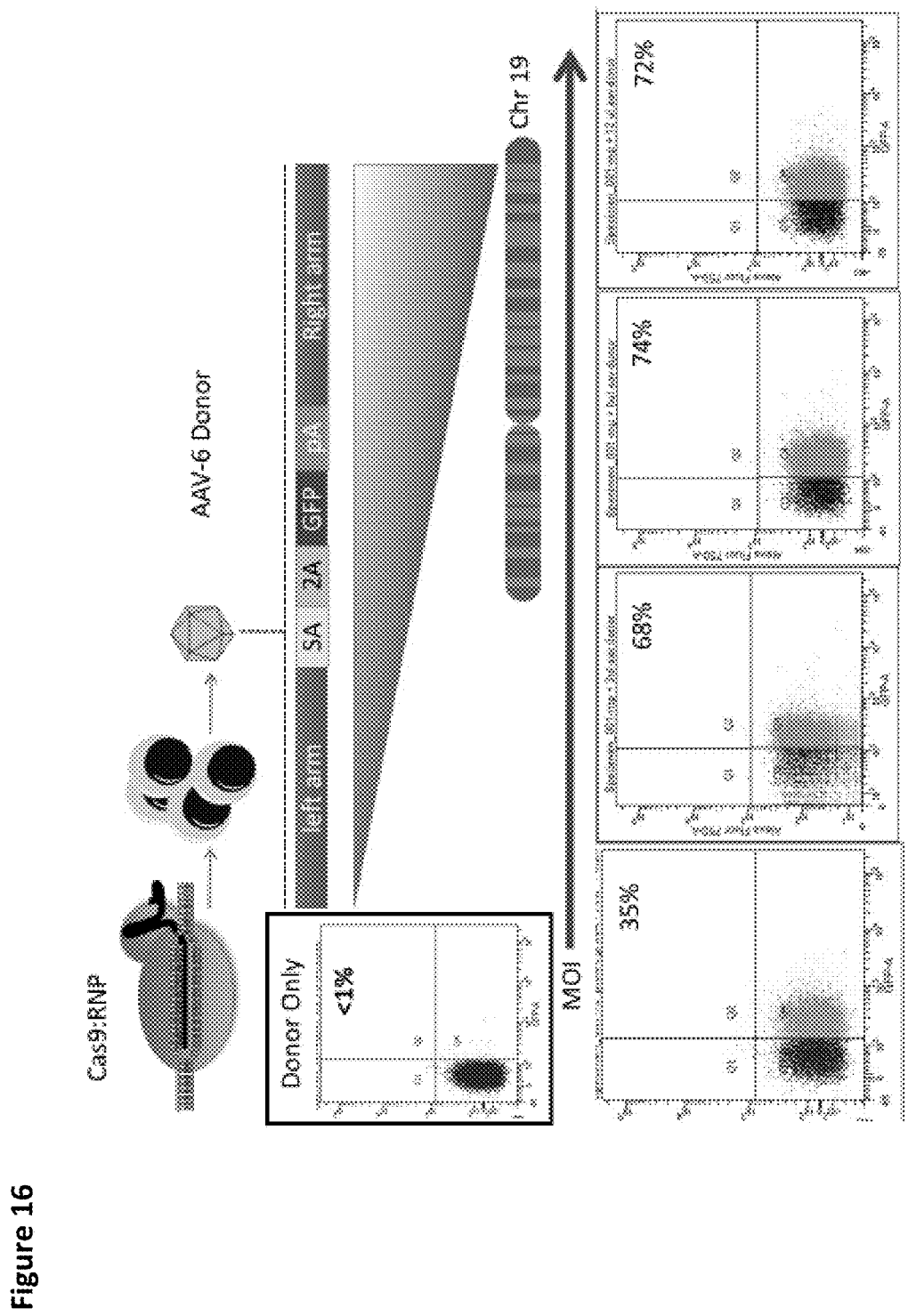
FIG. 16. HR template dose optimization. Cas9 RNP was delivered to cord blood CD34 cells followed by the AVV-borne homologous recombination donor specific for the AAVS1 locus. The donor contains homologous arms to the AAVS1 target site (left and right arms), a splice acceptor (SA), 2a peptide sequence, a GFP gene, and a polyadenylation signal (pA). Following electroporation the donor was added as AAV-6 particles at an MOIs of $1\times10^5$, $3\times10^5$, $5\times10^5$, or $1\times10^6$ was added immediately after electroporation. At 72 hours post gene transfer flow cytometry was performed for GFP expression that occurs only if HR has taken place.

FIG. 15 illustrates an alternative approach to generating repopulating hematopoietic stem and progenitor cells (HSPC) by modifying the conditions for homologous recombination (HR) using a donor molecule free of exogenous (i.e., foreign/drug/fluorescent genes). First, to define the optimal Cas9 configuration that drives the highest rates of HR in HSPC, Cas9 mRNA and Cas9 recombinant peptide delivered with a COL7A1 guide RNA (gRNA) were compared. The RNA molecules or ribonucleoprotein (RNP) complexes were delivered to healthy donor (HD) CD34+ umbilical cord blood cells via electroporation with the Neon transfection system (Thermo Fisher Scientific, Waltham, Mass.). Following this, a homologous recombination reporter template was delivered as an adeno-associated virus (AAV) serotype 6 particle. Molecular analysis showed that Cas9 RNP was more effective at mediating homologous recombination. FIG. 16 shows AAV donor dose optimization to determine the effective dose for HSPC homologous recombination.

Figure 17:
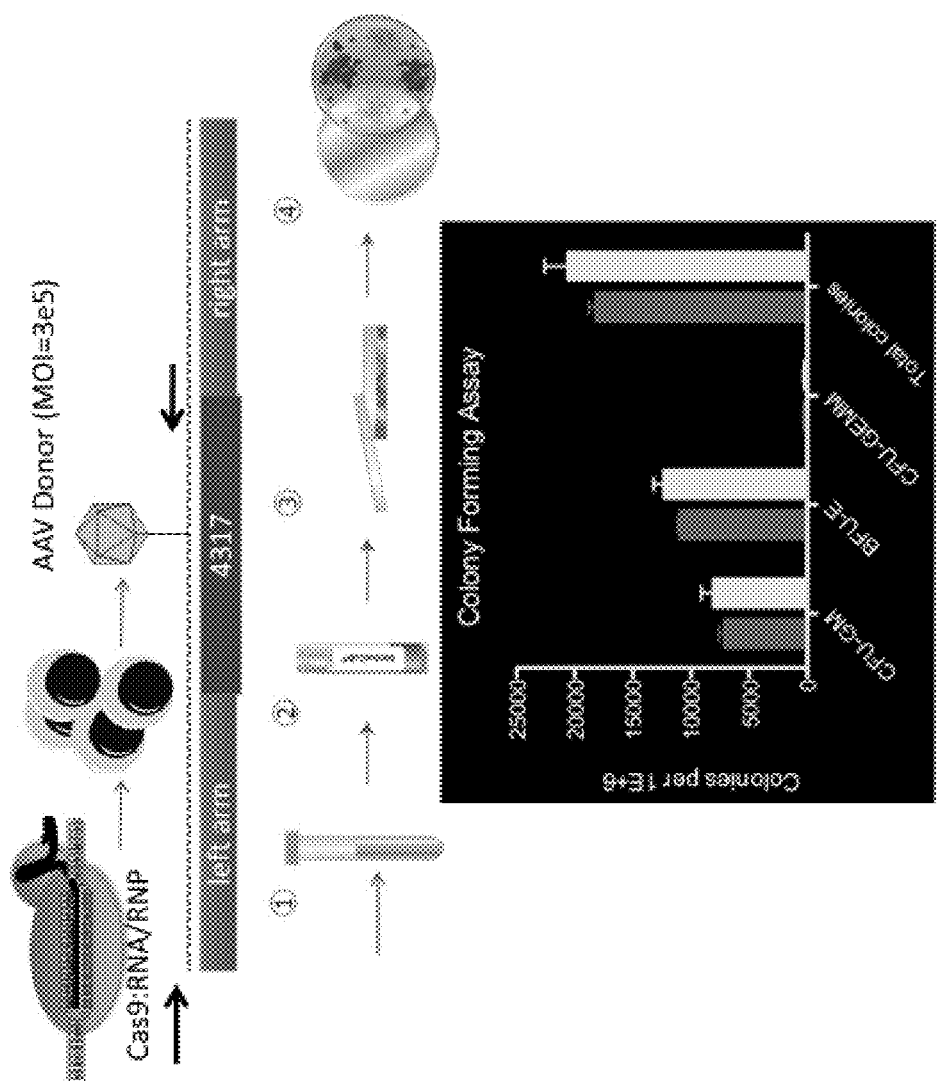
FIG. 17. COL7A1 donor and locus modification in human HSPCs. The Cas9 RNP is shown and the COL7A1 donor for correction of the 4317delC mutation is shown as a schema. The donor contains no foreign selectable markers, instead has silent DNA changes that retain the amino acid sequence (green box) and allow for the use of a donor specific PCR strategy that differentiates from modified vs unmodified COL7A1 modified loci. Cas9 RNP was delivered to cord blood CD34 cells followed by the homologous recombination donor as AAV-6 particles (MOI=3e5). At 48 hours post gene transfer the cells were plated in MethoCult (Stemcell Technologies, Inc., Vancouver, BC, Canada) for HSC colony forming unit (CFU) analysis. At bottom are the enumerated colonies from 4317 modified (yellow) and control (red) cells showing no difference between modified and unmodified CFU potential P=>0.5. These data show that COL7A1 locus modification maintains HSC CFU pluripotency.
Figure 18:
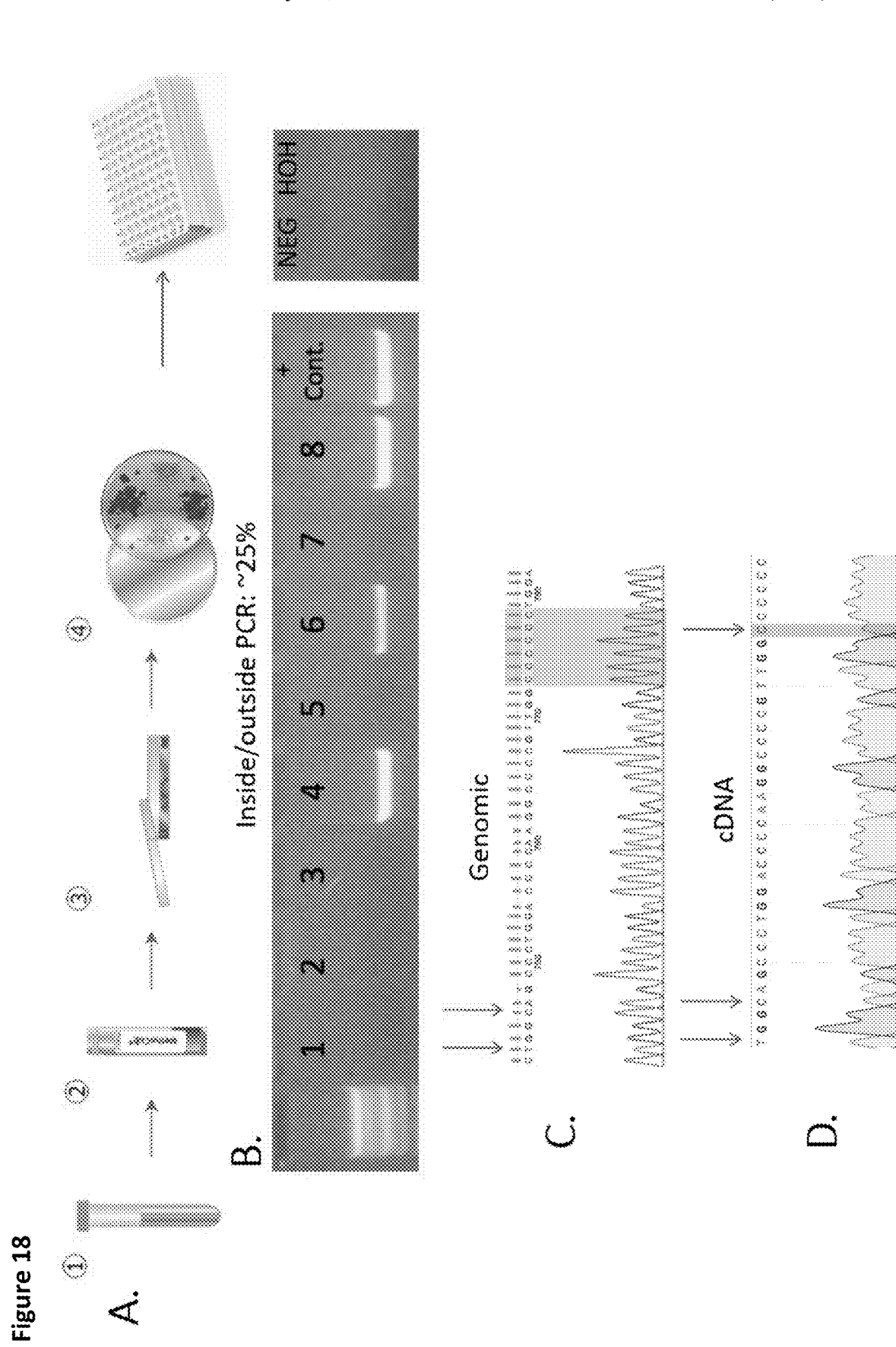
FIG. 18. COL7A1 locus modification frequency. (A). RNP modified HSPCs were plated in MethoCult and then 96 individual colonies were isolated for genomic DNA. (B) HR specific PCR. Colonies were screened using an inside/out allele specific PCR strategy. The forward primer is designed to bind to only the donor derived silent polymorphisms at the 4317 locus. The reverse primer binds at the COL7A1 locus outside of the donor arm of homology. A representative agarose gel of positive and negative PCR reactions are shown. Sanger sequencing of genomic (C; SEQ ID NO:61) or cDNA (D; SEQ ID NO:62) showing silent polymorphisms derived from the donor and the blue shaded base is the corrected cytosine.

FIG. 17 illustrates a donor free of selective/foreign genes to correct the 4317 delC mutation. Cas9 RNP was used to modify cells that were then plated in methylcellulose to show their ability to form hematopoietic colonies in semi-solid media. 96 individual colonies from the 4317-modified HSPCs were isolated and screened using donor specific primers. 25% of the colonies were modified by gene editing. RT-PCR was performed on cells in the bulk HSPC pool to show functional expression of COL7A1 donor-derived mRNA.

Gene repair in HSPC and cells from an RDEB patient is an exemplary method, and methods and materials similar or equivalent to those expressly described herein can be used in the practice or testing of the present technology. For example, this multilineage approach represents a strategy for broad therapeutic use in support of combinatorial systemic and localized interventions.

In one aspect, this disclosure describes a method that includes introducing into a cell that includes a genomic sequence in need of editing: a donor template polynucleotide including a polynucleotide that encodes an edited version of the genomic sequence in need of editing; a polynucleotide that encodes a clustered regularly interspaced short palindromic repeat associated (Cas) nuclease or nickase; and a guide RNA (gRNA). The nuclease and/or nickase allowed to cut at least one strand of the genomic sequence; and the edited version of the genomic sequence is allowed to replace the genomic sequence in need of editing, resulting in the production of a cell including a donor sequence.

A cell that includes a genomic sequence in need of editing can include an allogenic cell or a cell from a subject having a genetic defect. In some embodiments, the subject is a patient. The mutational profile can be heterogeneic with respect to position and can encompass homozygous or compound heterozygous alterations. In some embodiments, a cell that includes a genomic sequence in need of editing can include a mutation in the type VII collagen gene (COL7A1). A COL7A1 mutation can include a cytosine deletion including, for example, a 4317delC mutation. In some embodiments, the cell is preferably a fibroblast. In other embodiments the cell is an HSPC.

A donor template polynucleotide includes a polynucleotide that encodes an edited version of the genomic sequence in need of editing. For example, a donor template polynucleotide can encode an edited version of COL7A1. In some embodiments, the donor template polynucleotide preferably includes a double-stranded DNA template. In some embodiments, the donor template polynucleotide can include a drug resistance gene including, for example, an antibiotic resistance gene. An antibiotic resistance gene can include, for example, a puromycin drug resistance gene. In some embodiments, the drug resistance gene can be flanked by Lox sequences. In Example 3, an exemplary double-stranded DNA donor template was constructed that included homology arms of ~1 kb flanking a foxed puromycin drug resistance gene in such a way that it would be inserted into an adjacent intron for selection and subsequent cre recombinase-mediated removal (see, e.g., FIGS. 1C, 7A).

A polynucleotide that encodes a clustered regularly interspaced short palindromic repeat associated (Cas) nuclease or nickase can include any suitable nuclease or nickage. In some embodiments, the nuclease or nickase includes at least a portion of Cas9 or Cpf1. In some embodiments, a nuclease can generate double stranded DNA breaks while a nickase can cleave a single strand of DNA. In some embodiments, a nickase can include an inactivated Cas9 HNH domain.

The guide RNA (gRNA) is preferably specific for the genomic sequence in need of editing. For example, when the genomic sequence in need of editing includes a mutation in the type VII collagen gene (COL7A1), the gRNA can include at least one of: GTGCTGGGCTTCATAGTTCT TGG (SEQ ID NO:43), GGAGGCTGCGT-GCTGGGGGCAGG (SEQ ID NO:44), and GCCT-TGGGGTCCAGGGCTTCCGG (SEQ ID NO:45). In some embodiments, a predictive in silico modeling algorithm can be used to identify potential off target sites. In some embodiments, the putative off target sites can be screened to determine if off target editing occurs. For example, to determine if promiscuous CRISPR/Cas9 cutting occurred, putative off target sites were screened using a Surveyor assay (see, e.g., FIG. 9).

In some embodiments, the donor sequence replaces the genomic sequence in need of editing by homology-directed repair. In some embodiments, the donor sequence replaces the genomic sequence in need of editing by non-homologous end-joining.

In some embodiments, the method includes generating a clone from the cell including a donor sequence. For example, a population of cells can be plated at low density to allow for clonal selection, expansion, and/or screening. In some embodiments, the cells can be selected based on drug resistance. In some embodiments, the drug resistance gene can be removed after screening including, for example, by using a cre system (e.g., cre-mRNA).

In some embodiments, the cell including a donor sequence or a clone derived from the cell including a donor sequence can be reprogrammed to obtain an induced pluripotent stem cell (iPSC). In some embodiments, the cell can be reprogrammed to obtain a transgene-free, gene-corrected, karyotypically normal iPSC. In some embodiments, the cell is preferably reprogrammed using Sendai virus-based reprogramming. In some embodiments, the iPSC demonstrates hypomethylation of OCT4 and/or NANOG gene promoters. In some embodiments, teratomas derived from an iPSC will contain representative tissues from all three germ layers.

In some embodiments, the method includes differentiation of the iPSC. For example, the iPSC can be differentiated to generate a keratinocyte, a mesenchymal stem cell (MSCs), and/or a hematopoietic progenitor cell.

In some embodiments, including, for example, when the iPSC is differentiated to generate a keratinocyte, the method can include two-dimensional culture of an iPSC in media comprising at least one of retinoic acid and bone morphogenic protein 4 (BMP-4). In some embodiments, the method can include culture of an iPSC in defined keratinocyte serum-free media (DKSFM) and/or CnT-07 media. In some embodiments, a keratinocyte population can be enhanced by exploiting the keratinocyte cells' ability to rapidly attach to collagen I and IV coated plates. A keratinocyte can include a keratin-expressing epidermal cell. An iPSC-derived keratinocyte can include, for example, a cell positive for keratin-5 (Krt5), keratin-14 (Krt14), keratin-15 (Krt15), and/or transcription factor p63 (see, e.g., FIG. 2). In some embodiments, an iPSC-derived keratinocyte can exhibit rapid attachment to type IV collagen-coated tissue culture plates, elevated expression of mRNAs associated with commitment to the keratinocyte lineage, and/or elevated expression of Col7A1 mRNA (see, e.g., FIG. 2B) compared to undifferentiated iPSCs). In some embodiments, an iPSC-derived keratinocyte exhibits characteristic epithelial morphology and expresses keratinocyte-specific genes and transcription factors.

In some embodiments, including, for example, when the iPSC is differentiated to generate a mesenchymal stem cell (MSC), the method can include exposing an iPSC to media including, for example, MSC media (alpha-MEM plus 5% horse serum and either 5% fetal bovine serum or 10% human serum). In some embodiments, the media can include at least one of platelet-derived growth factor (PDGF)-AB, basic fibroblast growth factor (bFGF), and epidermal growth factor (EGF). In some embodiments, the method can include exposing the cell to a matrigel substrate, a gelatin-coated plastic tissue culture vessel, or both. In some embodiments, the method includes exposing an iPSC undergoing differentiation to media that includes a Rho-associated protein kinase (ROCK) inhibitor. In some embodiments, an MSC can express at least one of CD73, CD90, and CD105. In some embodiments, an MSC can undergo differentiation to a adipocyte, a chondrocyte, and/or an osteoblast in vitro or in vivo. In some embodiments, an iPSC-MSC can be indistinguishable from a primary human MSC in its morphology, cell surface antigen profile, and its capacity for tri-lineage differentiation (i.e., its capacity for differentiation to an adipocyte, a chondrocyte, and/or an osteoblast). In some embodiments, an iPSC-derived MSC retains the ability to self-renew in culture. Preferably, the gene-corrected iPSC-derived MSC, in contrast to an uncorrected, parental fibroblast, shows expression of the donor sequence. For example, COL7A1-corrected iPSC-derived MSCs but not parental uncorrected fibroblasts showed collagen type VII protein expression (FIG. 12C). In some embodiments, iPSC-derived MSCs exhibit at least one of a spindle morphology, expression of CD73, CD90, and/or CD105, and the ability to undergo adipogenic, chondrogenic, and osteogenic differentiation in vitro in a manner indistinguishable from bone marrow-derived MSCs.

In some embodiments, including, for example, when the iPSC is differentiated to generate a hematopoietic progenitor cell, the method can include embryoid body (EB) formation. In some embodiments, the EB formation is preferably feeder cell-free. In some embodiments, the media can include at least one of BMP4, VEGF, bFGF, CHIR99021, and SB431542, and hematopoietic cytokines (including, for example, Flt3-ligand, SCF, IL-6, and/or IL-3). In some embodiments, the method can include exposing an iPSC to a serum free media. A serum free media can include, for example, animal-free polyvinyl alcohol essential lipid (APEL); human serum albumin-based media, TeSR1; or STEMPRO34. In some embodiments, an iPSC can be exposed to a mix/ratio of at least two of APEL, TeSR1, and STEMPRO34. In some embodiments, the method can include inhibiting at least one of Activin/Nodal and GS3Kβ related pathways. In some embodiments, the differentiated iPSCs are preferably CD34+. In some embodiments, the differentiated iPSCs are preferably negative for the mesenchymal marker CD73 and/or the vascular marker CXCR4.

In some embodiments, an iPSC-derived hematopoietic progenitor is at least one of CD45+, CD34+, and CD38−; in some embodiments, an iPSC-derived hematopoietic progenitor is preferably CD45+CD34+CD38−. In some embodiments, the method includes co-culture with vascular stroma including, for example, a human vascular stromal endothelial cell population that expresses the adenovirus E4ORF1 gene or delta/notch like ligand components. In some embodiments, the method includes co-culture with VeraVec endothelial cells. In some embodiments, an iPSC-derived hematopoietic progenitor that has undergone co-culture with vascular stroma after the EB stage exhibits an increase in colony frequency and an expansion in multilineage potential compared an EB that did not undergo co-culture with vascular stroma (see, e.g., FIG. 5E).

In some embodiments, the method includes introducing a gene-corrected cell, e.g., a cell including a donor sequence into a subject having a genetic defect. In some embodiments, a cell including a donor sequence includes a fibroblast including a donor sequence or an iPSC-derived cell including a donor sequence. In some embodiments the donor sequence contains a foreign marker gene (e.g., but not limited to an antibiotic resistance gene or a fluorescent gene) that promotes preferential outgrowth/selection. In other embodiments, the donor is free of foreign (i.e., non-native) sequence (e.g., SEQ ID NO:63). In some of these embodiments, the donor may contain a silent polymorphism that results in the incorporation of a DNA sequence that differs from the consensus human genome sequence but maintains the wild type amino acid code. In some embodiments, the gene-corrected cell is derived from a cell from a subject having a genetic defect. For example, a COL7A1-corrected fibroblast or a COL7A1-corrected iPSC-derived could be derived from a patient having a COL7A1 mutation and then reintroduced into the patient. In some embodiments, the subject is a patient having recessive dystrophic epidermolysis bullosa (RDEB). In some embodiments, producing a gene-corrected cell can be used to treat RDEB. In some embodiments, the cell is an autologous or allogeneic hematopoietic stem or progenitor cell with long term engraftment and blood constituent formation/production potential.

The present invention is illustrated by the following examples. It is to be understood that the particular examples, materials, amounts, and procedures are to be interpreted broadly in accordance with the scope and spirit of the invention as set forth herein.

EXAMPLES

Example 1. Efficient CRISPR/Cas9-Mediated Knockout of Col7a1 in NOD/SCID IL2Rgamma-Null Mice by Pro-Nuclear Injection Current immunocompetent Col7a1-null mouse models of recessive dystrophic epidermolysis bullosa (RDEB) are not amenable to pre-clinical studies involving the transplantation of human cells. To address this limitation, pro-nuclear injection and CRISPR/Cas9 technology were combined to disrupt the Col7a1 gene in immunodeficient NOD/SCID IL2Rgamma-null (NSG) embryos; a strain that is highly permissive to adoptive transfer of human cells. Tandem guide RNAs (gRNA) targeting exon two of the Col7a1 gene were co-delivered with Cas9 into single-cell NSG embryos via pronuclear injection. Using low and high doses, pups exhibiting phenotypic manifestations of RDEB were obtained at rates of 34% (n=35) and 83% (n=79), respectively. Complete absence of type VII collagen in skin and mucosa of blistered pups was confirmed by immunofluorescence microscopy. There was no evidence of somatic cell mosaicism indicating that the molecular disruption occurred at the single cell stage. A range of CRISPR/Cas9 induced indel patterns that included mutation at each site individually and concurrently were observed, as well as large deletions spanning both target sites. Non-blistered pups with single allele frameshift disruptions were utilized to establish breeding colonies. The short lifespan of Col7A1-null mice necessitates carefully timed matings, and the number of homozygous-null animals is limited by Mendelian genetics. Using pro-nuclear injection and CRISPR/Cas9, large numbers (>30) of RDEB-NSG pups born were routinely obtained within narrow time-windows (<12 hours), thereby facilitating complex human cellular transplant experiments. The ease with which CRISPR/Cas9 can be directed to disrupt discreet genomic loci with high fidelity will facilitate the rapid production of disease model mice on the NSG background without the need to undertake time-consuming and expensive backcrossing, greatly accelerating pre-clinical trials testing the safety and efficacy of cellular therapies.

Example 2. MiR-29 Regulates Type VII Collagen in Individuals with Recessive Dystrophic Epidermolysis Bullosa (RDEB)

Regulation of type VII collagen, expressed from COL7A1 and diminished or absent in severe generalized RDEB, is incompletely understood. As tumor growth factor beta (TGF-β) is elevated in RDEB and as TGF-β signaling leads to a decrease in miR-29, how miR-29 regulates COL7A1 was investigated. Fibroblasts were transfected with miR-29 family mimics and observed a reduction in COL7A1 expression in both RDEB dermal fibroblasts (miR-29a: 0.533, miR-29b: 0.626, miR-29c: 0.383, all p≤0.05) and normal dermal fibroblasts (miR-29a: 0.433, miR-29b: 0.292, miR-29c: 0.279, all with a p≤0.05) relative to the mimic control. To delineate the critical components of this event, miR-29 mimics and a luciferase vector containing the 3' UTR of COL7A1 were co-transfected, and a decrease in luciferase activity in comparison to controls was observed (miR-29A: 0.508, miR-29B: 0.414, miR-29C: 0.456, all p≤0.05). This capacity of miR-29 regulating COL7A1 directly through targeting its 3' UTR was confirmed by mutating the two seed sequences for miR-29 in the COL7A1 3' UTR (the complementary sequences between miR-29 and the COL7A1 3' UTR required for regulation) and demonstration that this eliminated the negative regulation of miR-29 on the COL7A1 3' UTR. In search of more complete mechanism of action, the impact of miR-29 on transcription factor SP1 that controls basal expression of COL7A1 was also investigated. A miR-29-mediated decrease in SP1 expression in both RDEB dermal fibroblasts (miR-29A: 0.709, miR-29B: 0.871, miR-29C: 0.818, all p≤0.05) and normal dermal fibroblasts (miR-29A: 0.756, miR-29B: 0.575, miR-29C: 0.650, all p≤0.05) was noted. These data demonstrate novel, miR-29-mediated, mechanism of COL7A1 regulation at both a transcriptional and post-transcriptional level, via targeting the 3' UTR of COL7A1 and through regulating SP1 transcriptional activity. Taken together, these data indicate that TGF-β, miR-29 and SP1 are linked in the pathophysiology of RDEB, and suggest novel targets for amelioration of its clinical manifestations.

Example 3. Skin Engraftment and Type VII Collagen (C7) Expression after Allogeneic Hematopoietic Cell Transplantation (HCT) for Generalized Severe Recessive Dystrophic Epidermolysis Bullosa (RDEB)

In 2010, the results of allogeneic hematopoietic cell transplantation (HCT) in six patients with RDEB was reported and suggested that increased C7 expression paralleled better wound healing. As of January 2016, 30 patients aged 5 months to 20 years have been treated by allogeneic HCT with follow up ranging from 2 months to 8 years. At 100, 180, and 365 days after HCT, the impact of allogeneic HCT on C7 expression was assessed by immunofluorescence staining, AFs by transmission and immunoelectron microscopy, resistance to blister formation by skin exposure to negative pressure, chimerism by polymerase chain reaction, and wound healing by clinical photography. A durable improvement in mucocutaneous integrity was demonstrated in 17 of 18 patients alive and engrafted. Out of 30 recipients, mucocutaneous chimerism >5% was observed in 24. An increase in C7 expression was documented in 10 subjects, with C7 detectable before and after HCT in an additional 6. High-density, thick, and/or arching AFs were detected in 16. In 13 patients, localization of C7 at the sites of AF-like structures at the dermal-epidermal junction was demonstrated, providing evidence for generation of new AFs. For the entire group, the probability of survival at two years was 77% (CI, 54-90%). Patients with severe generalized RDEB can have an objective and sustained improvement in mucocutaneous integrity following HCT.

Example 4. CRISPR/Cas9-Based Genetic Correction for RDEB

Research Subject and Cell Line Derivation

Patient-derived samples were obtained following parental consent and approval from the University of Minnesota Institutional Review Board. A 4-mm skin punch biopsy was collected followed by mincing the skin tissue and submerging in complete DMEM media with 20% FBS, non-essential amino acids, antibiotics, and glutamax all from Invitrogen, (Carlsbad, Calif.). Primary fibroblasts were maintained in complete DMEM media under hypoxic (<2% $O_2$) conditions.

CRISPR/Cas9 Reagent and Donor Construction

The *S. pyogenes* hCas9 plasmid was a gift from Dr. George Church (Addgene plasmid #41815) (Mali et al. *Science* 339, 823-826 (2013)), and the gRNAs were assembled into a plasmid with a U6 promoter and polIII termination signal (Osborn et al. *Hum Gene Ther* 26, 114-126 (2015)). The donor sequence was comprised of left and right arms of homology that were assembled by amplification from the human genome with:

```
Left arm F:
                                    (SEQ ID NO: 1)
CCTGACCTCTTCACCTCCTCAGGGCTTCC, Left Arm R:
                                    (SEQ ID NO: 2)
GGGCCACACCTCACTCCCAAAGATACCAGG.
```

The Right arm was amplified with RT Arm1 F: AGGGTCATGGGGTCGTCATCTGTTTTCTAGGG (SEQ ID NO:3) and Reverse: AACTATGAAGCCCAGCACCCAACCACTGCCCCAGG (SEQ ID NO:4) that overlapped with a synthesized fragment containing the corrective base (underlined in bold) and two silent polymorphisms (shaded) CTCTCCTGGGGCAGTGGTTGGGTGCTGGGCTTCATAGTTCTTGCTCATATTTTTACTCAC TTCTTCCTAGGGTCTTCCTGGC AGCCCTGGACCCCAAGGCCCCGTTGGCCCCCCTGGAA AGAAAGGAGAAAAAGTAGGAAGGCTGACTTGATGATGTCCCAGTTCTGGGGTGGGAG GCTGCGTGCTGGGGGCAGCCTCCCTTCGGTCTTCCCACCCGTGTGTTTCTCCTTCAGGGTGACTC (SEQ ID NO:5). The remainder of the right donor arm was amplified with:

```
Right Arm2 F:
                                    (SEQ ID NO: 6)
CACCCGTGTGTTTCTCCTTCAGGGTGACTC
and reverse:
                                    (SEQ ID NO: 7)
GGGCAAGAAGTCAGAACCAGAAAGGGCACAGC.
```

These fragments were assembled into a plasmid containing the left donor arm followed by a floxed PGK puromycin cassette by Gibson assembly to complete the donor (Gibson et al. *Nat Methods* 6, 343-345 (2009)).

Gene Transfer

Primary fibroblasts (200,000) were electroporated with 1 μg each of the Cas9 and gRNA plasmids and 5 μg of the donor using the following settings on the Neon Transfection System (Invitrogen): 1500 V, 20 ms pulse width, and a single pulse (Osborn et al. *Mol Ther* 21, 1151-1159 (2013)).

Surveyor Nuclease

Genomic DNA was isolated 48 hours after Cas9/gRNA electroporation and amplified for with Surveyor 13F (CCATGACCCTCATCACTCCT (SEQ ID NO:8)) and Surveyor 708R primers (TTTGGGGGTTCAGAGATTTG (SEQ ID NO:9)) and incubated with the Surveyor nuclease (Integrated DNA Technologies, Coralville, Iowa) (Guschin et al. *Methods in Molecular Biology* (*Clifton* 649, 247-256 (2010)) and resolved on a 10% TBE PAGE gel (Invitrogen).

Off Target Analysis 293T cells were transfected using Lipofectamine 2000 and the Cas9 nuclease or nickase (500 ng) and guide RNA plasmid (500 ng). Genomic DNA was isolated 72 hours post gene transfer and PCR amplified with 4317 131F: TCCCAAAGTCCTTGAAATCC-3' (SEQ ID NO:10)) and 4317 777R: GCCCACCATATTCAGAATCC-3' (SEQ ID NO:11)) for on-target site amplification. Off-target sites were identified using the MIT CRISPR Design Tool (available on the world wide web at crispr.mit.edu) and were amplified with following primers:

```
ACAP3F:
                                    (SEQ ID NO: 12)
ACGGCCTTGTACAGAACTGG,

ACAP3R:
                                    (SEQ ID NO: 13)
GTGCTTTCGCTCCATCTCAC,

GRK6F:
                                    (SEQ ID NO: 14)
CCAGAGGAGCCTTGAGTTTG,
```

GRK6R:
CTACCCAGCCCCCTTACTTC, (SEQ ID NO: 15)

E2F2F:
TGGTACGTCGAGGGTCCTAA, (SEQ ID NO: 16)

E2F2R:
CCTTGGAGGCTACTGACAGC, (SEQ ID NO: 17)

SEC23AF:
GCTACCTCTCCTCCCTCCTC, (SEQ ID NO: 18)

SEC23AR:
CCACCGTTTTCCACATCTTT, (SEQ ID NO: 19)

CARD10F:
GGCTCATCCGTAACCTGCTA, (SEQ ID NO: 20)

CARD10R:
GGGCAACCTGGAGATACAGA, (SEQ ID NO: 21)

SYTL1F:
TTTTGTCGAGATGGGGTCTC, (SEQ ID NO: 22)

SYTL1R:
GGGGACAGTGCATAATCTGG, (SEQ ID NO: 23)

FADS3F:
AGATGAACCACATCCCCAAG, (SEQ ID NO: 24)

FADS3R:
TGGACAAGGGTAGGCATAGG, (SEQ ID NO: 25)

FAM3DF:
AAGAATCAGGAAGCCCAGGT, (SEQ ID NO: 26)

FAM3DR:
GTCTCAAACAGCCCAGCTTC, (SEQ ID NO: 27)

MLLT1F:
GAGACCAAGCTGGAAAGCAC, (SEQ ID NO: 28)

MLLT1R:
AGCTCAGAACCTCAGGACCA, (SEQ ID NO: 29)

MYO1EF:
CATTCCTCTCTGCCACCTTC, (SEQ ID NO: 30)

MYO1ER:
TGTTCGCCGATTCCTTTATT, (SEQ ID NO: 31)

TIE1F:
AGAGGTGACACAGCCCTCAT, (SEQ ID NO: 32)

TIE1R:
AGGGTCTTCTCCCAGTCAGG, (SEQ ID NO: 33)

SHANK2F:
CTTTGGGTCCCTGTTGAGAC, (SEQ ID NO: 34)
and

SHANK2R:
GAAGACGTGCTCCATCCCTA. (SEQ ID NO: 35)

PCR conditions were: 94° C.×2 minutes followed by 40 cycles of 94° C.×40 seconds, 58° C.×40 seconds, and 68° C.×1 minute with AccuPrime DNA polymerase (Thermo-Fisher Scientific, Waltham, Mass.). PCR products were denatured and renatured and assayed by Surveyor nuclease (Integrated DNA Technologies) and subsequent resolution on a 10% TBE PAGE gel (ThermoFisher Scientific) (Osborn et al. *Hum Gene Ther* 26, 114-126 (2015); Guschin et al. *Methods in Molecular Biology* (Clifton 649, 247-256 (2010)). All gel images used the same exposure times.

Selection and HDR Analysis

80% confluent fibroblasts that had undergone electroporation were exposed to 0.2 µg/mL puromycin and then plated at low density for clonal derivation. Individual cells were segregated in cloning disks and expanded for HDR analysis using an inside-out PCR. A primer inside the donor (GCCACTCCCACTGTCCTTTCCT (SEQ ID NO:36)) and outside the right homology arm (GGGCAAGAAGTCAGAACCAG (SEQ ID NO:37)) were amplified, cloned into the pCR 4 TOPO vector (Invitrogen) and sequenced by the Sanger method to confirm HDR. cDNA correction was demonstrated by amplification of a product with cDNAF: GTGACAAAGGCGATCGTG (SEQ ID NO:38) and cDNAR: GTCCCCGTGGGCCCTGC (SEQ ID NO:39) followed by sequencing.

PGK Puromycin Removal

Cre recombinase mRNA (TriLink Biotechnologies, San Diego, Calif.) was electroporated into iPSC clones at a dose of 1 µg using the conditions noted above, and excision was confirmed by PCR and Sanger sequencing.

iPSC Generation and Teratoma Assay

Gene-corrected fibroblasts (or un-corrected cells as a control) were reprogrammed to iPSCs as described (Tolar et al. *J Invest Dermatol.* 131, 848-856 (2011); Tolar et al. *J Invest Dermatol.* 133, 562-565 (2013)) with Sendai virus delivery of the reprogramming factors (Fujie et al. *PLoS One* 9, e113052 (2014)). Karyotype, gene expression, and immunofluorescence as part of quality assurance and control were also performed as detailed elsewhere (Tolar et al. *J Invest Dermatol.* 131, 848-856 (2011); Tolar et al. *J Invest Dermatol.* 133, 562-565 (2013)). iPSCs contained in matrigel were implanted onto the hind flank of NSG mice (n=3-5) until a palpable mass formed. Teratoma tissue was excised for histological examination following embedding and staining by hematoxylin and eosin.

Differentiation of iPSCs to Keratinocytes iPSCs were maintained feeder-free on Geltrex-coated (Thermo Fisher Scientific, Waltham, Mass.) tissue culture plastic in TesR1 (Stemcell Technologies, Inc., Vancouver, BC, Canada). For keratinocyte differentiation, mid-passage iPSCs at ~50% confluency in 6-well plates had media changed to defined keratinocyte-SFM media supplemented with 25 ng/ml BMP-4 (Bio-Techne, Minneapolis, Minn.) and 1 µM retinoic acid (RA) (Stemcell Technologies, Inc., Vancouver, BC, Canada) for the first 96 hours, at which point the BMP4 and RA were removed followed by media changes every 72 hours thereafter until epithelial cell morphology became apparent (~10 days). At this timepoint, the media was switched to Cnt-07 (CELLnTEC, Bern, Switzerland) and the cells cultured until confluency. The cells were pre-treated with ROCK inhibitor (Y-27632, VWR) for at least 1 hour and passaged using Accutase (STEMCELL Technologies) onto 10 cm² tissue culture plates coated with collagen I/collagen IV, where rapid attachment-mediated enrichment of Krt14+ cells was performed as previously described. Resultant iPSC-keratinocyte cultures were cultured in Cnt-07 media containing 10 micromolar (µM) ROCK inhibitor until first media change after plating (CELLnTEC AG, Bern, Switzerland).

Differentiation of iPSCs to MSCs iPSCs were maintained feeder-free on Geltrex-coated tissue culture plastic in TesR1 (Stemcell Technologies, Inc., Vancouver, BC, Canada). Differentiation to MSCs was initiated by transferring mid-passage iPSCs at 50% confluency to MSC medium, which consisted of Minimal Essential Medium Alpha supplemented with 5% fetal bovine serum, 5% horse serum, and 10 ng/ml each of human Platelet-Derived Growth Factor-AB (PDGF-AB), Epidermal Growth Factor (EGF), and Fibroblast Growth Factor-basic (bFGF) (all from PeproTech, Rocky Hill, N.J.). Media was changed every 48 hours until cells with fibroblastic morphology were apparent and cultures neared confluency. At this point, MSC cultures were pre-treated with 10 µM ROCK inhibitor for at least 1 hour and dissociated using a 50:50 mixture of Accutase and 0.25% Trypsin-ethylenediaminetetraacetic acid (EDTA) incubated at 37° C. When cells had detached, the Accutase/trypsin mixture was diluted with 2× volume of phosphate-buffered saline (PBS)+1% FBS+3 mM EDTA to prevent clumping. Cells were centrifuged at 400×g for five minutes and re-plated onto gelatin-coated plates in growth media plus cytokines containing 5 µM ROCK inhibitor to enhance plating efficiency. Between passages 3-5, cultures can be weaned off of ROCK inhibitor during passage.

Maintenance and Differentiation of Human iPSCs to Hematopoietic Progenitors

Human iPSC lines were maintained on Matrigel- or Geltrex-coated plastic ware in TesR1 (Stemcell Technologies, Inc., Vancouver, BC, Canada). For differentiation, hiPSCs were cultured at around 80-90% confluency, followed by EB generation, as described previously (Ng et al. *Nat Protoc* 3, 768-776 (2008); Osborn et al. *Stem Cells Dev* (2016)). Briefly, the undifferentiated hiPSCs were dissociated with Accutase (Stemcell Technologies, Inc., Vancouver, BC, Canada) treatment. Aggregates were resuspended in APEL-differentiation medium (Stemcell Technologies, Inc., Vancouver, BC, Canada), supplemented with BMP-4 (20 ng/mL) and bFGF (5 ng/mL) and cultured in non-tissue culture treated plates. After 42 hours, developing EBs were collected and resuspended in APEL-differentiation media supplemented with BMP-4, bFGF, CHIR99021 (3 µM, Stemgent, Lexington, Mass.), and SB431542 (6 µM, Selleck Chemicals, Houston, Tex.).

After 24 hours, EBs were collected and resuspended in either 60% APEL-differentiation medium plus 40% STEM-SPAN II medium (Stemcell Technologies, Inc., Vancouver, BC, Canada) for vascular induction, or 100% APEL-differentiation medium for T-lineage differentiation; both supplemented with VEGF (20 ng/mL), bFGF (5 ng/mL), IL-3 (20 ng/mL), Flt3L (20 ng/mL), and SCF (100 ng/mL) and cultured for another 5-6 days. Cultures were maintained in a 5% $CO_2$/5% $O_2$/90% $N_2$ environment. At day 8 or 9, EBs were harvested, washed once with PBS, and dissociated using Accutase and 0.25% trypsin EDTA mixture until no visible clumps observed. CD34+ cells were enriched using Easy-Sep CD34+ isolation kit (Stemcell Technologies, Inc., Vancouver, BC, Canada).

Vascular Induction

For vascular induction, $1\times10^5$ purified EB-derived CD34+ cells were plated onto 85% confluent VeraVec HUVEC (Angiocrine Bioscience, San Diego, Calif.) in StemSpan II supplemented with the following: SCF (200 ng/mL), Flt3L (10 ng/ml), TPO (30 ng/mL), IL-11 (5 ng/mL), IGF-1 (25 ng/mL), bFGF (5 ng/mL), VEGF (5 ng/mL), EPO (2 IU/mL), IL-6 (10 ng/mL), IL-3 (30 ng/mL), BMP-4 (10 ng/mL), and losartan (100 µM). Co-cultures were maintained for 7-9 days.

T-Lineage Differentiation

For T lineage differentiation, $1\times10^5$ purified CD34+ cells were plated onto confluent OP9-DLL4 cells for about 3-4 weeks and passaged every 4-5 days as described previously (Kennedy et al. *Cell Rep* 2, 1722-1735 (2012)). All recombinant factors are human and were purchased from R&D Systems (Minneapolis, Minn.).

Colony-Forming Unit Assay

Cells were placed in MethoCult according to the manufacturer's instructions (Stemcell Technologies, Inc., Vancouver, BC, Canada). Colonies were enumerated by an experienced analyst using light microscopy at low magnification (4× objective).

Western Blotting

Cellular lysates in RIPA lysis buffer (ThermoFisher Scientific) were electrophoresed using the XCell SURELOCK Mini-Cell Electrophoresis System with a NuPAGE Novex 3-8% acetate gel (Thermo Fisher Scientific, Waltham, Mass.). Proteins were transferred to a nitrocellulose membrane and stained with the 4D2 mouse monoclonal anti-human collagen 7 antibody (Santa Cruz Biotechnology, Dallas, Tex.). Secondary staining was performed with a goat anti-mouse horse radish peroxidase conjugated antibody (Santa Cruz Biotechnology) and detection with the Super-Signal West Pico Chemiluminescent Substrate (Thermo Fisher Scientific, Waltham, Mass.).

The overall experimental schema is detailed in FIG. 1 and provides a strategy that employed patient-derived fibroblasts that were precisely modified with a CRISPR/Cas9 mutation-specific reagent. Cells were induced to pluripotency with Sendai viral, footprint free reprogramming and differentiated into effector lineages.

CRISPR/Cas9 Gene Correction

Three candidate gRNAs proximal to the 4317delC COL7A1 gene mutation characterized by a single cytosine deletion (FIGS. 6(A) and (B)) were generated for testing with the *S. pyogenes* Cas9 that was delivered as DNA expression cassettes (FIGS. 6(C) and (D)). Using the Surveyor assay (Osborn et al. *Hum Gene Ther.* 26, 114-126 (2015)), all three candidates resulted in cleavage products consistent with Cas9 activity and DNA repair by non-homologous end joining (NHEJ) (FIGS. 6(E) and (F)). Because fibroblasts are a major contributor of C7 in the dermis, CRISPR/Cas9 reagents for gene correction were deployed using a targeting strategy comprised of three plasmids: Cas9 nuclease or nickase, the C7 gRNA, and an exogenous donor repair template (FIG. 1C, FIG. 7A). The Cas9 nuclease generates double stranded DNA breaks while the nickase version, due to inactivation of the Cas9 HNH domain, cleaves a single strand of DNA (Bannwarth et al. *Hum. Mutat.* 25, 575-582 (2005)). A double-stranded DNA donor template was constructed consisting of homology arms of ~1 kilobases flanking a floxed puromycin drug resistance gene in such a way that it would be inserted into an adjacent intron for selection and subsequent cre recombinase-mediated removal (FIG. 1C, FIG. 7A). To allow for unambiguous determination of donor-derived homology-directed repair (HDR), silent polymorphisms within the right donor arm were included (FIG. 7A). The donor fragment and the nuclease or nickase version of Cas9 and gRNA 2 were electroporated into fibroblasts that were then puromycin-selected in bulk. The puromycin resistant cells were screened for HDR using an 'inside-out' PCR strategy, with a primer inside the donor and outside of the right homology arm.

Bulk population cells were plated at low density to allow for clonal selection, expansion, and screening, and 17 total clones were obtained. Four clones that received the Cas9 nickase, and eight treated with Cas9 nuclease, showed HDR at the genomic level (FIG. 1D, FIG. 7B). The puromycin cassette was subsequently removed using cre-mRNA, which resulted in a small loxp footprint in the intron (FIG. 7C). Screening at the cDNA level showed gene correction and donor polymorphism presence in COL7A1 gene transcripts (FIG. 7D). These data show the ability of the CRISPR/Cas9 to mediate gene repair in primary fibroblasts obtained from an RDEB patient that, importantly, retained a normal morphology and karyotype (FIGS. 8(A) and (B)).

An important consideration for the employment of programmable gene editing reagents is their specificity for the intended gene target. Because of the presence of sequences of partial homology to the bona fide target a predictive in silico modeling algorithm was used to identify potential off target sites (Table 1). To determine whether promiscuous CRISPR/Cas9 cutting occurred the putative off target sites were screened using the Surveyor assay. One off target site in the ACAP3 gene (FIG. 9) that functions as a GTPase activating protein (Stelzl, U, et al. *Cell* 122, 957-968 (2005)) was observed. Importantly, the nickase version of Cas9 that preferentially promotes homology-directed repair (HDR) (Osborn et al. *Hum Gene Ther.* 26, 114-126 (2015)) did not show any mutagenic non-homologous end joining (NHEJ) at this locus (FIG. 9) and, therefore, nickase-corrected clones were employed for reprogramming to pluripotency.

TABLE 1 shows off-target activity analysis. CRISPR Design Tool-identified Intragenic off-target sites were assessed. The mismatches between the COL7A1 target site and the putative off-target sites are shown in bold and underlined. Target genes and their functions are shown. At right are the results of the Surveyor analysis in Cas9 nuclease-treated or nickase-treated cells. The +/− sign indicates whether locus modification as assessed by the Surveyor assay was observed or not.

| Target | Gene | Function | Surveyor (nuclease/nickase) |
|---|---|---|---|
| GGAGGCTGCGTGCTG GGGGCAGG (SEQ ID NO: 44) | COL7A1 | anchoring fibril | +/− |
| ACAGGCTGCATGTTG GGGGCTGG (SEQ ID NO: 49) | ACAP3 | GTPase activation | +/− |
| GGGGGCCTCGGGCTG GGGGCTAG (SEQ ID NO: 50) | GRK6 | G protein kinase | −/− |
| GGGGGCAGGCTGCTG GGGGCAGG (SEQ ID NO: 51) | E2F2 | transcription factor | −/− |
| GGCGGCGGCGGGCTG GGGGCTGG (SEQ ID NO: 52) | SEC23A | zinc ion binding | −/− |
| GGAAGGTGGGTGCTG GGGGCTGG (SEQ ID NO: 53) | CARD10 | apoptosis signaling | −/− |
| TGGGGCTACGTCCTG GGGGCCAG (SEQ ID NO: 54) | SYT11 | exocytosis/transport | −/− |
| TGAGTGTGGGTGCTG GGGGCCAG (SEQ ID NO: 55) | FADS3 | lipid metabolism | −/− |
| GGAGGTTGGGGGCTG GGGGCTGG (SEQ ID NO: 56) | FAM3D | insulin secretion | −/− |
| GGTGAGTGAGTGCTG GGGGCAGG (SEQ ID NO: 57) | MLLT1 | DNA binding | −/− |
| AGGGGCTGGGGGCTG GGGGCTGG (SEQ ID NO: 58) | MYO1E | ATP binding | −/− |
| TGGGGCTGGGCGCTG GGGGCCAG (SEQ ID NO: 59) | TIE1 | ATP binding | −/− |
| GAGGGCCGCGTCCTG GGGGCGGG (SEQ ID NO: 60) | SHANK2 | synaptic protein | −/− |

RDEB Gene-Corrected iPSCs

Using Sendai virus-based reprogramming, transgene-free, gene-corrected, karyotypically normal iPSCs were obtained (FIGS. 8(C) and (D)). Resultant iPSC clones were positive for pluripotent markers at the protein (FIG. 10) and gene expression levels (FIG. 11A). As further verification of successful reprogramming, the OCT4 and NANOG gene promoters were observed to be hypomethylated, and in vivo teratomas derived from gene-corrected iPSCs contained representative tissues from all three germ layers. (FIGS. 11(B) and (C)).

These results demonstrate that CRISPR/Cas9 genome modification and Sendai virus reprogramming allow for precision repair and iPSC generation. This population of cells was subsequently employed to derive therapeutic cell types suitable for cellular therapies for RDEB.

Production of Keratinocytes from Gene-Corrected iPSCs

Treatment of the chronic wounds experienced by RDEB patients could be bolstered by the localized delivery of gene-corrected keratinocytes. To demonstrate that iPSCs derived from CRISPR/Cas9 gene-corrected RDEB fibroblasts are capable of differentiating into therapeutically relevant cell populations in vitro, protocols to produce keratinocytes under fully defined, feeder-free conditions were used (Itoh et al. *Proc Natl Acad Sci. USA* 108, 8797-8802 (2011); Umegaki-Arao, N., et al. *Sci Transl Med.*

6, 264ra164 (2014); Kogut et al. *Methods Mol Biol.* 1195, 1-12 (2014)). Two-dimensional culture of iPSCs in the presence of retinoic acid and bone morphogenic protein-4 (BMP-4) resulted in the formation of cells with characteristic epidermal morphology (FIG. 2). Compared to undifferentiated iPSCs, differentiation cultures enriched for keratin-expressing epidermal cells by rapid attachment to type IV collagen-coated tissue culture plates exhibited significantly elevated expression of mRNAs associated with commitment to the keratinocyte lineage as well as elevated expression of Col7A1 mRNA (FIG. 2B). Concordant with keratinocyte morphology and mRNA expression profile, iPSC-derived keratinocyte cultures contained a high frequency of cells positive for keratin-5 (Krt5), keratin-14 (Krt14), and transcription factor p63 (FIG. 2C). These data show the ability of CRISPR/Cas9 gene-corrected iPSCs to successfully differentiate into keratinocytes in vitro under fully defined, xeno-free culture conditions amenable for clinical translation.

Production of MSCs from Gene-Corrected iPSCs

Mesenchymal stem cells (MSCs) are mesoderm-derived, fibroblastic cells present within many tissues, including bone marrow and adipose tissue. There is substantial evidence that MSCs or MSC-derived cells can enhance wound healing via modulation of wound microenvironment, immunomodulation, or by direct integration into cutaneous tissues after transplant. At present, targeted gene editing in primary human MSCs has not been demonstrated.

Figure 3:
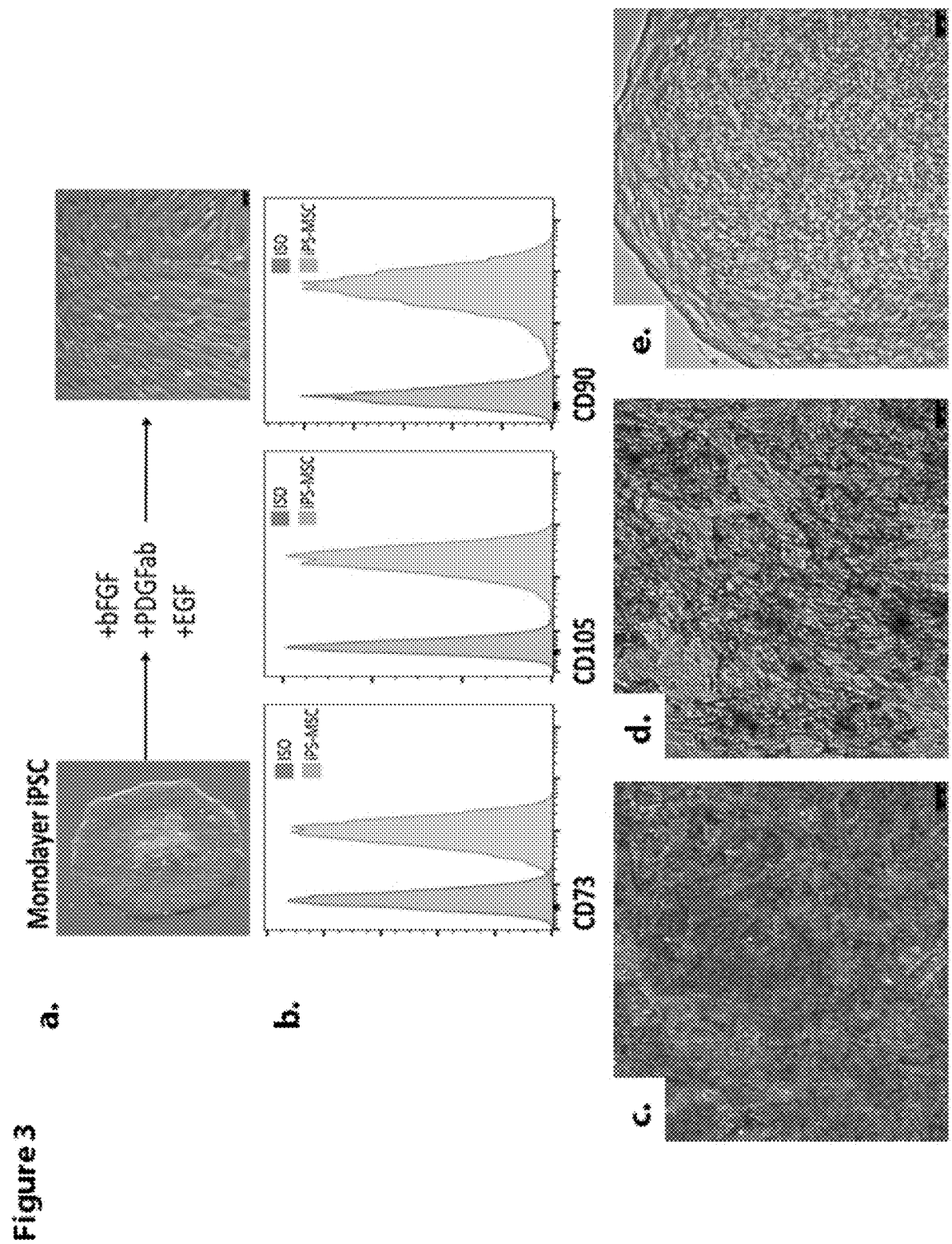
FIG. 3. One exemplary embodiment of mesenchymal stem cell (MSC) derivation. (A) MSC differentiation. Monolayer iPSCs were subjected to Fibroblast Growth Factor-basic (bFGF), Platelet-Derived Growth Factor-AB (PDG-Fab), and Epidermal Growth Factor (EGF), resulting in differentiation to a cell population with spindle-shaped morphology (right). (B) Fluorescence-activated cell sorting (FACS) analysis. Passage 3 MSCs were analyzed for cell surface expression of CD73, CD105, and CD90 (n=3 experiments), and histogram analysis is shown in blue. Isotype antibody control FACS histograms are shown in pink.

Directed differentiation of COL7A1 gene-corrected iPSCs to MSCs in vitro was pursued (Lian et al. *Circulation* 121, 1113-1123 (2010)). COL7A1 gene-corrected iPSCs were exposed to MSC media supplemented with platelet-derived growth factor (PDGF)-AB, basic fibroblast growth factor (bFGF), and epidermal growth factor (EGF) until iPSC colony morphology was lost and outgrowth of cells with fibroblastic morphology was observed (FIG. 3A). At this stage the cells were passaged from the matrigel substrate to gelatin-coated plastic tissue culture vessels. In contrast to Lian et al. *Circulation* 121, 1113-1123 (2010), Rho-associated protein kinase (ROCK) inhibitor was used during passaging, and cell survival and re-plating during passages 1-3 was observed to be substantially enhanced in the presence of Rho-associated protein kinase (ROCK) inhibitor, allowing for more consistent establishment of robust iPSC-MSC cultures capable of expansion with minimal senescence (FIG. 12A). Between passages 3 and 5, uniform iPSC-MSC cultures were obtained and flow cytometric analysis demonstrated the expression of MSC markers CD73, CD90, and CD105 (FIG. 3B, FIG. 12B). Furthermore, COL7A1-corrected iPSC-derived MSCs were able to undergo robust tri-lineage differentiation to adipocytes, chondrocytes, and osteoblasts in vitro (FIG. 3(C)-(E)); a defining characteristic of primary MSCs (Dominici et al. *Cytotherapy* 8, 315-317 (2006)). Collectively, these data show that COL7A1 gene-corrected iPSCs are capable of producing MSCs in vitro, and that these iPSC-MSCs are indistinguishable from primary human MSCs in their morphology, cell surface antigen profile, and their capacity for tri-lineage differentiation and retain the ability to self-renew in culture (FIG. 3, FIG. 12). Moreover, the gene-corrected iPSC-derived MSCs but not parental uncorrected fibroblasts showed collagen type VII protein expression (FIG. 12C).

Production of Definitive Hematopoietic Progenitors from Gene-Corrected iPSCs

Figure 13:
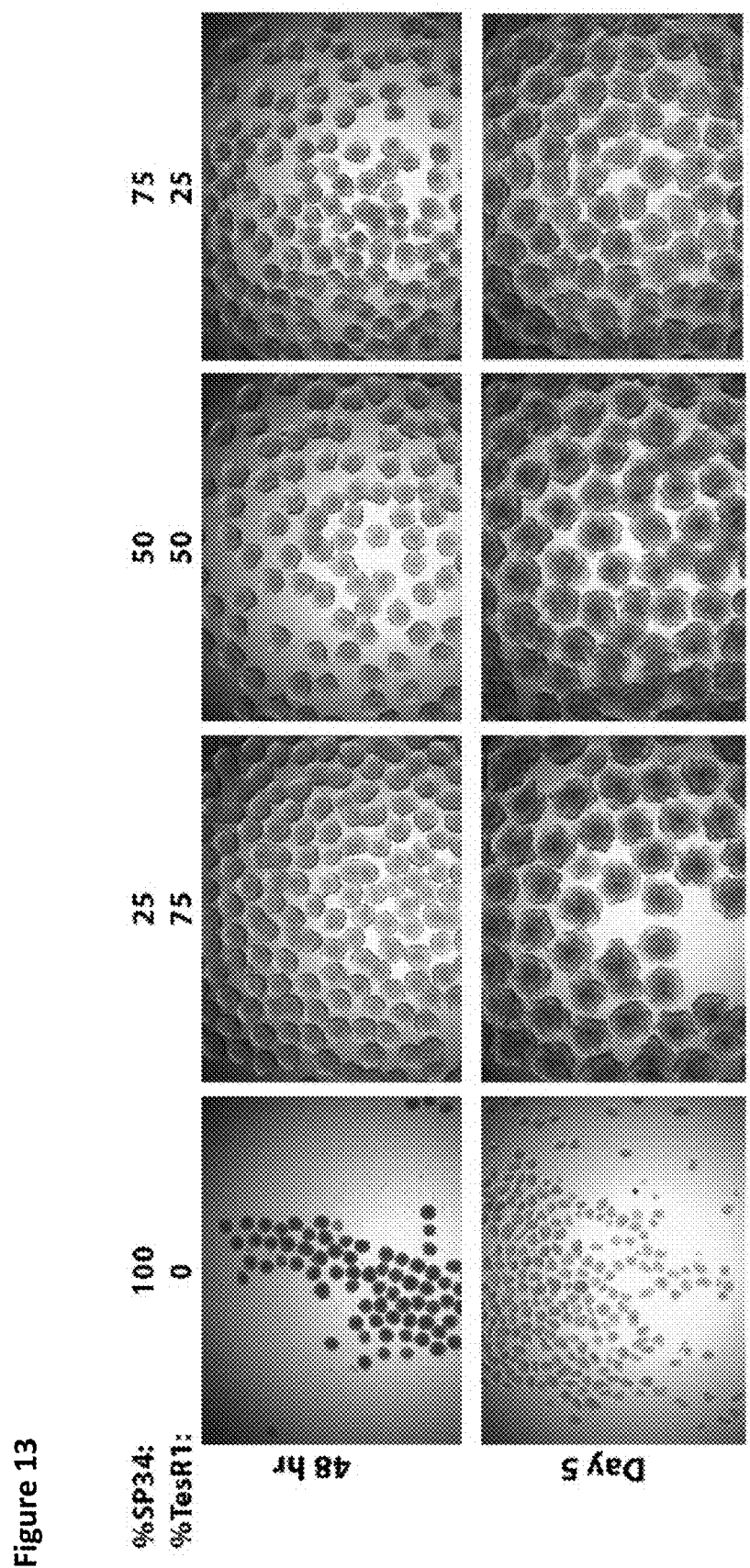
FIG. 13. Inclusion of Tesr1 in STEMPRO34 (also referred to herein as SP34) enhances EB formation and growth. Embryoid bodies were formed in StemPro34 media supplemented with indicated amounts of Tesr1 and imaged at indicated time points. Images are at 50× magnification.

Although cutaneous blistering is the most apparent pathology observed in patients with RDEB, it is the systemic manifestations—including mucosal blistering—that are often the most destructive and life-threatening and which cannot be resolved by localized grafting of epidermal cell types such as keratinocytes or fibroblasts. The amelioration of systemic RDEB pathology by HCT is associated with a substantial risk of morbidity and mortality during the preparative and post-transplant period. Therefore, the generation of gene-corrected HSPCs would be a highly desirable approach for autologous therapy. While targeted gene-editing in severe combined immune deficiency-repopulating human HSPCs has been demonstrated, the efficiency is not yet robust enough for models such as RDEB that do not confer a selective or proliferative advantage to the modified cell(s). Therefore, to advance the understanding of in vitro HSPC generation an effort to develop a translational workflow under serum and feeder-free conditions was undertaken. Protocols for serum-free hematopoietic differentiation have been described, yet in each of these reports the starting iPSCs are cultured on xenogeneic murine feeder cells, which is suboptimal for clinical translation (Ditadi et al. *Nat Cell Biol.* 17, 580-591 (2015); Kennedy et al. *Cell Rep.* 2, 1722-1735 (2012); Sturgeon et al. *Nat Biotechnol.* 32, 554-561 (2014)). Implementing these protocols to feeder-free iPSC cultures was met with limited success, and embryoid body formation, growth, and production of CD34+ hemogenic progenitors was observed to be poor (FIG. 13). In light of these observations the differentiation protocol was optimized to allow robust generation of hematopoietic progenitors under fully defined, serum-free, xeno-free conditions. The nutrient-rich, human serum albumin-based media TeSR1 was employed for maintenance of feeder-free cells, and embryoid bodies (EB) were generated in the presence of the hematopoietic progenitor medium STEMPRO34. Hematopoietic induction frequency is highest when cells transit through an EB stage, and the abrupt transition from TeSR1 to STEMPRO34 was observed to result in poor hematopoietic cell derivation (FIG. 13). Therefore, EB formation in STEMPRO34 supplemented with dilutions of TeSR1 was pursued and EB formation was found to be enhanced substantially (FIG. 13). In support of the ultimate goal of feeder-free iPSCs with differentiation carried out in fully defined media, the conditions for elimination of TeSR1 media that contains undefined human serum albumin were sought. Animal-free polyvinyl alcohol essential lipid (APEL) (Ng et al. *Nat Protoc* 3, 768-776 (2008)) was employed as a base media that allowed for sustained growth of EB after TeSR1 removal and robust production of CD34+ hematopoietic progenitors at day 8 (FIG. 4A). As part of this procedure, the commitment phase of blood development was modulated by combining Activin/Nodal inhibition and GS3Kβ inhibition at the mesoderm phase of differentiation in order to bias the system toward definitive hematopoiesis. A substantial portion of the CD34+ fraction at day 8 was negative for the mesenchymal marker CD73 and the vascular marker CXCR4, representing a robust population of hemogenic precursors (FIG. 4B) (Ditadi, A et al. *Nat Cell Biol* 17, 580-591 (2015)). The definitive potential of EB-derived CD34+ cells was further confirmed via demonstration of T-lineage specification upon co-culture with OP9-DLL4 (FIG. 14). However, when assessed directly in vitro by methylcellulose-based hematopoietic colony-forming unit (CFU) assay, the day 8 EB CD34+ fraction exhibited a markedly limited myeloid potential, indicating that further maturation was required to complete ultimate specification to committed HSPC (FIG. 4C). Given the complex niche in which definitive HSPC arise during development, a means of recapitulating that environment in vitro was sought. To accomplish this a supportive human vascular stromal endothelial cell population that expresses the adenovirus E4ORF1 gene and has been shown to support endothelial to HSPC derivation in vitro was employed. (Gori et al. *J Clin Invest* 125, 1243-1254 (2015); Sandler et al. *Nature* 511, 312-318 (2014)). EB-derived mature CD34+ cells were generated as before (FIG. 5A), and at day 8 purified CD34+ hemogenic precursors were co-cultured with the vascular stroma and subsequently underwent endothelial to hematopoietic transition to form rounded hematopoietic cells that contained a subpopulation of CD45+CD34+CD38- hematopoietic progenitors (FIGS. 5(B) and (C)). In CFU assays, day 8 EB-derived CD34+ cells that underwent vascular induction showed a broader colony differentiation potential (FIG. 5D). In aggregate, day 8 EBs with 7-day co-culture on a supportive vascular endothelial matrix resulted in both a significant increase in colony frequency and an expansion in multilineage potential compared to day 8 EBs alone (FIG. 5E). These data demonstrate that COL7A1-corrected iPSCs represent a platform for the in vitro production of definitive hematopoietic progenitors capable of producing multiple blood lineage cell types in CFUs that represent an advance toward true HSPC in vitro generation.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

```
Sequence Listing Free Text
Selection-free donor sequence
UPPER CASE: intron sequences
lower case: exon sequences
                                                        SEQ ID NO: 63
TCCCAGAGGC AGGGAAGCCC TCTGCCTTGT CGCTGCCCTT GTGCCTGGAA TTGGGCTCTG

TGAAGCTCTG AGGGGCCATT TCTCTGCCTC ACTGTTCCAC CCCCAATAAC ACTTGGGGGT

CAGTGGGGTA GGCGACCCCT TGTTGATGGG GTGAGGCCCC TCCAGCAAAC CAGGGGCCTT

GGGGGAGGGT CCCTTCCTGT CCTGACCTCT TCACCTCCTC AGggcttccc tggagcagat gggcgtccag gcagccctgg ccgcgccggg aatcctggga ccctggagc cctggccta aagGTGAGCA AGCCTTGTCC TGCAGGTCAG GGTGGGCGCT GCCTGAGTGG GTGGGTGGC TCCGACTGTT CTGCCTCTGG CCTCCATTTG CAGggctctc cagggttgcc tggccctcgt ggggacccgG TAAGGTGCCT TCCCTTCTTT GCTCTCTAAG TGTCTTCCCA GGGTTCTTCC

ACAGGGTGGG AGCCTGGGGT GGTGGTGCAG TGCCCACGTT GACATTCGCC TGAGCCCAAG

CACCACCCTC TGCTCTGTTT CGTCCTCAGg gagagcgagg acctcgaggc ccaaaggggg agccgGTAGG TGAAGGGGGA AGGGAGGCGG CCGGGATGTC CCAGGGAGGA GCAGGACTGC

CCCACACCAG ACCCTGTGCA GGGCCTAAGG CGCGAATAGG AATAGCTGGA CATGTCTAGG

GGCTTCTTCC AGCTCAAGGC CCCCATAGCC TGAATCCTGC CCACTGCTCT CTGTCCTTAC

AGggggctcc cggacaagtc atcggaggtg aaggacctgg gcttcctggg cggaaagggg accctggacc atcgGTAAGT GCAGGGTATG TGGAGGCAAG TGATGTGTAG TGGGGGGACC

AACACGAGGG GGGCGAGAGT GAGGTCTGTG GGGTTGCACC TTATACTTTG TCTCCTCCAT

CAGggccccc ctggacctcg tggaccactg ggggacccag gacccgtgg cccccagggg cttcctggaa cagccatgaa gGTGACAGCC TCATGAGTGC CATGTGATGC AGAGACCTGG

TGACCCCATT TGAACCCACA TAACCCCTGC CAGTTACTCT GGCCCTTGTG ACCCTTTGAT

TACCCCCATC CTCACCATGA CGCCTCAGTT CTCCCAAAAT CCTTGAAATC CAATTGGACC

CCATGACCCT CATCACTCCT GGTATCTTTG GGAGTGAGGT GTGGCCCAGG GTCATGGGGT

CGTCATCTGT TTTCTAGggt gacaaaggcg atcgtgggga gogGTAAGT GAGGGACAGG

TTGTGCTAGG GGTGGCTTGG AGTCTGATTC CCCTGTTCAT TCCCTGACCT GCTGTTCTCT

CCCAGggtcc ccctggacca ggtgagggcg gtatcgcccc aggagagcct gggctgccgG

TGAGGGGCCT TGAGGCTCTG CTGGGGGCCC TGCTCAGGGG TGTGGGTCTC TCCTGGGGCA
```

-continued

```
GTGGTTGGGT GCTGGGCTTC ATAGTTCTTG CTCATATTTT TACTCACTTC TTCCTAGggt cttcctggca gccctggacc ccaaggcccc gttggccccc ctggaaagaa aggagaaaaa

GTAGGAAGGC TGACTTGATG ATGTCCCAGT TCTGGGGTGG GAGGCTGCGT GCTGGGGGCA

GCCTCCCTTC GGTCTTCCCA CCCGTGTGTT TCTCCTTCAG ggtgactctg aggatggtgc ccctggcctg cctggccaac ctgggtctcc gggtgagcag GTGAGTGGAG GGGCCAGGGA

TTCTGAATAT GGTGGGCACA GCTCCAGCCC CTACCTCAAT CATCAACCAC TGCTCCATCC

TCATGCCCAA ACCCAAATCT CTGAACCCCC AAATTCATCC CTTCCAGggc ccacggggac ctcctggagc tattggcccc aaaGTGAGTA CCAGTTGGGG GATTCAGGTG TGAGGGGTGC

TACTCTGGGC TCCCCATGGT GTTAGGGGAG GCTGGAAGAT AAGGAGATAA GAGTTCCCTC

CAGGTCAGAG GTCGTGGTTT TGGAGGGGGT GGTTGGAGTT TGGGACCCCT TGTCTGGGGT

TTGACGTTCA AGCCCCGCCA CCAACCCTCT CTCTCTCTGT CTTTCTCTCA CCCTCTCTCT

TCAGggtgac cggggctttc cagggcccct gggtgaggct ggagagaagG TAAGTGCAAC

CTGGGGGGTG CCAAGGGCCC TGGAGGATCT GGGCCCAACT CAGCTCTGAC CTCTTCTTTT

CCATCAGggc gaacgtggac ccccaggccc agcgggatcc cggGTAAACC CACTGGCTGC

AATGCTCATA CCAGCTGACC TGGCTGTGCC CTTTCTGGTT CTGACTTCTT GCCCTTGACC

CCTGCTACCC CTGCTCCTCA CCCCTCCTCA ATGACCACTT ATCCCTGCTG ATACAGGCTC

TAACCCTCAG CCCCAGGGAC CTGGCTTTGA ACCTCTGACC CTGCTGAACT GACCTTGATT

TTCACTGACC TGGTCTCTGT TCTCCTGCCA AGTCTTACCC CTGCCAACCT AAATCCCAAT

CTTCCCTGAC CCCTCTCCAG CCCCCACCCC AGCCTCTAGC CCTGTCTGTC CATATCCCCC

GTCCCCACCC ACCTGCACAG CTCTTCCCTT CCTCTCCTCC AGgggctgcc aggggttgct ggacgtcctg gagccaaggg tcctgaaGTG AGTCTGTGAC TGTGGTGGGA CCAGGAGTGG

GACTTTTGTG TGTCCCTCCC CTTTCCCTTC CCCTCCTGGG CTCACACTTT CTCTACATTC

AGgggccacc aggacccact ggccgccaag gagagaagGT GGGTCCTCGG CTGGGGGTGG

CACTGTCTGG TACTAGGGAT GTGGCAGATG GGACACTGGG ATTTTGGGCT CCTAGGTGAC

TCCCTGACCT GTCCCTGCTC ctatcctctc tccacagggg gagcCTGGTC GCCCTGGGGA

CCCTGCAGTG GTGGTGAGTG ACGGGAGGAT GGCGCTCTGA GCACAGCACA GCCCTTGAGC

AGTGACCCTC CTATAGAACA CTATCTGGGC TGTGATTCCA CAGTGCTGGG CCCGTGAGCA

GGCTGGGAGC TCTGCGGCTC TCCTTCTGCT AGAACCTGCC CCCAGACTCT TGGCTATGAT

CCTGTGACCC CAAGACCGCC ATGCAGGTCA TGAGCTCTTT GTGTCAGTCC ATTTTGTATA

ACCCCTTCCC TGCTGTCAGC GGTGACTCTG TGACTTCTGG GCGGGGACTG AGCTGTATGA

CTTCCAATTC CATGTGACCT CCATTCCAAT GAAGACTTTG ATCATACAAC CCCAAGGCAG

GGCCAAGCTG TATCTGTCCT GTTTGTTTTC AGggacctgc tgttgctgga cccaaaggag aaaagGTAAG CCTGGTATGG GGCAAGGGGA GGTTTCTACA GGGTTGAGGT CTAGGTCATA

GGGCCTATCT ATGGGACTTG GGGGGTCACA GGACTTGCTG GGTCAGGGGG TTAACTGGAG

CCTGGGACTA GCACTGATGG TCTTTGTCAC CTCCAGggag atgtggggcc cgctgggccc agaggagcta ccggagtcca aggggaacgg GTAAGTGAAG CGAAGTGTTT AGGGGGCAGT TGGTGAAGGT TGTCTTCCTG ACTTCTTATC CTTCCATCCA CAGggcccac ccggcttggt tcttcctgga gaccctggcc ccaagggaga ccctggagac cggGTGAATC AATGTGGGAA

TGGGGAGTGT GACAGAGGGA GATGAGGTGG TGGGACCCTG ACTAAGTCCT
```

What is claimed is:

1. A method comprising:
introducing into a cell that comprises a genomic sequence in need of editing:
- a donor template polynucleotide that comprises a polynucleotide that encodes an edited version of the genomic sequence;
- a polynucleotide that encodes a clustered regularly interspaced short palindromic repeat associated (Cas) nuclease or nickase; and
- a guide RNA (gRNA), wherein the gRNA comprises at least one of:

```
                         (SEQ ID NO: 43)
GTGCTGGGCTTCATAGTTCTTGG, (SEQ ID NO: 44)
GGAGGCTGCGTGCTGGGGGCAGG,
and (SEQ ID NO: 45)
GCCTTGGGGTCCAGGGCTTCCGG;
``` allowing the nuclease or nickase to cut at least one strand of the genomic sequence; and
allowing the edited version of the genomic sequence to replace the genomic sequence in need of editing to produce a cell comprising a donor sequence.

2. The method of claim 1, wherein the cell that comprises a genomic sequence in need of editing is a fibroblast.

3. The method of claim 1, wherein the genomic sequence in need of editing encodes a portion of the type VII collagen gene (COL7A1).

4. The method of claim 1, wherein the Cas nuclease or nickase comprises at least a portion of Cas9.

5. The method of claim 1, wherein the donor template polynucleotide comprises a drug resistance gene.

6. The method of claim 1, the method further comprising: generating a clone from the cell comprising a donor sequence.

7. The method of claim 1, the method further comprising: reprogramming a cell comprising a donor sequence to obtain an induced pluripotent stem cell (iPSC).

8. The method of claim 7, wherein reprogramming the cell comprises Sendai virus-based reprogramming.

9. The method of claim 7, the method further comprising differentiation of the iPSC to form an iPSC-derived cell.

10. The method of claim 9, wherein differentiation of the iPSC comprises differentiation to at least one of a keratinocyte, a mesenchymal stem cell (MSCs), or a hematopoietic progenitor cell.

11. The method of claim 9, the method comprising two-dimensional culture of an iPSC in media comprising at least one of retinoic acid and bone morphogenic protein 4 (BMP-4).

12. The method of claim 9, the method comprising exposing an iPSC to media comprising at least one of platelet-derived growth factor (PDGF)-AB, basic fibroblast growth factor (bFGF), and epidermal growth factor (EGF).

13. The method of claim 9, the method comprising exposing an iPSC to media comprising a Rho-associated protein kinase (ROCK) inhibitor.

14. The method of claim 9, the method comprising embryoid body (EB) formation.

15. The method of claim 14, wherein EB formation comprises exposing an iPSC to a serum free media.

16. The method of claim 14, the method comprising inhibiting at least one of Activin/Nodal and GS3Kβ.

17. The method of claim 14, the method comprising co-culture with vascular stroma.

18. The method of claim 1, the method further comprising isolating the cell that comprises a genomic sequence in need of editing from a subject prior to introducing into the cell the donor template polynucleotide, the polynucleotide that encodes a Cas nuclease or nickase, and the gRNA.

19. The method of claim 1, the method further comprising introducing the cell comprising a donor sequence or an iPSC-derived cell comprising a donor sequence into a subject.

20. The method of claim 19, wherein the donor sequence of the cell comprising the donor sequence or the donor sequence of an iPSC-derived cell comprising the donor sequence is free of marker genes.

* * * * *